US007960584B2

(12) United States Patent
Suh et al.

(10) Patent No.: US 7,960,584 B2
(45) Date of Patent: *Jun. 14, 2011

(54) COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

(75) Inventors: Young-Ger Suh, Seoul (KR); Hee-Doo Kim, Seoul (KR); Hyeung-Geun Park, Seoul (KR); Uh Taek Oh, Seoul (KR); Yong-Sil Lee, Seoul (KR); Seol Rin Park, Pusan-si (KR); Chong Hyon Ryu, Jeonju-si (KR); Young-Ho Park, Seoul (KR); Song Seok Shin, Yongin-si (KR); Sun-Young Kim, Seoul (KR); Jin Kwan Kim, Suwon-si (KR); Yeon Su Jeong, Yongin-si (KR); Ki-Wha Lee, Seoul (KR); Jin Kyu Choi, Suwon-si (KR); Kyung Min Lim, Suwon-si (KR); Hyun Ju Koh, Gunpo-si (KR); Joo Hyun Moh, Yongin-si (KR); Sung-Il Kim, Yangju-si (KR); Joon Ho Bae, Seoul (KR)

(73) Assignee: Amorepacific Corporation, Seoul (KR)

( * ) Notice: Subject to any disclaimer, the term of this patent is extended or adjusted under 35 U.S.C. 154(b) by 625 days.

This patent is subject to a terminal disclaimer.

(21) Appl. No.: 11/909,144

(22) PCT Filed: Mar. 17, 2006

(86) PCT No.: PCT/KR2006/000988
§ 371 (c)(1),
(2), (4) Date: Nov. 15, 2007

(87) PCT Pub. No.: WO2006/101321
PCT Pub. Date: Sep. 28, 2006

(65) Prior Publication Data
US 2008/0234383 A1 Sep. 25, 2008

Related U.S. Application Data

(60) Provisional application No. 60/663,269, filed on Mar. 21, 2005.

(30) Foreign Application Priority Data

Mar. 19, 2005 (KR) ........................ 10-2005-0022986

(51) Int. Cl.
*C07C 311/02* (2006.01)
(52) U.S. Cl. ............. 564/56; 564/99; 514/595; 514/605
(58) Field of Classification Search .................. 514/595, 514/605; 564/56, 99
See application file for complete search history.

(56) References Cited

U.S. PATENT DOCUMENTS

2003/0153596 A1 8/2003 Suh et al.
2004/0157865 A1 8/2004 Codd et al.

FOREIGN PATENT DOCUMENTS

| WO | WO 02/16318 A1 | 2/2002 |
| WO | WO 03/049702 A2 | 6/2003 |
| WO | WO 03/095420 A1 | 11/2003 |
| WO | WO 2005/003084 A1 | 1/2005 |

OTHER PUBLICATIONS

Gunthorpe et al. Current Pharmaceutical Design 2008, 14, 32-41.*
Schafer et al. Drug Discovery Today 2008, 13 (21/22), 913-916.*
Horig et al. Journal of Translational Medicine 2004, 2(44).*
Mezey, E. et al., "Distribution of mRNA for vanilloid receptor subtype 1 (VR1), and VR1-like immunoreactivity, in the central nervous system of the rat and human", PNAS, vol. 97, No. 7, pp. 3655-3660, Mar. 28, 2000.
Cortright, D. et al., "The Tissue Distribution and Functional Characterization of Human VR1", *Biochemical and Biophysical Research Communications*, vol. 281, pp. 1183-1189, Feb. 6, 2001.
Nagy, I. et al., "The role of the vanilloid (capsaicin) receptor (TRPV1) in physiology and pathology", *European Journal of Pharmacology*, vol. 500, pp. 351-369, Aug. 17, 2004.
Petersen, K. et al., "Capsaicin evoked pain and allodynia in postherpetic neuralgia", *PAIN*, vol. 88, pp. 125-133, Apr. 11, 2000.
Walker, K. et al., "The VR1 Antagonist Capsazepine Reverses Mechanical Hyperalgesia in Models of Inflammatory and Neuropathic Pain", *The Journal of Pharmacology and Experimental Therapeutics*, vol. 304, No. 1, pp. 56-62, Sep. 9, 2002.
Kim, S. et al., "Transient Receptor Potential Vanilloid Subtype 1 Mediates Cell Death of Mesencephalic Dopaminergic Neurons In Vivo and In Vitro", *The Journal of Neuroscience*, vol. 25(3), pp. 662-671, Jan. 19, 2005. Kamei, J. et al., "Role of vanilloid VR1 receptor in thermal allodynia and hyperalgesia in diabetic mice", *European Journal of Pharmacology*, vol. 422, pp. 83-86, May 15, 2001.
Chan, C. et al., "Sensory fibres expressing capsaicin receptor TRPV1 in patients with rectal hypersensitivity and faecal urgency", *Lancet*, vol. 361, pp. 385-391, Feb. 1, 2003.
Yiangou, Y. et al., "Vanilloid receptor 1 immunoreactivity in inflamed human bowel", *Lancet*, vol. 357, pp. 1338-1339, Apr. 28, 2001.
Holzer, P., "TRPV1 and the gut: from a tasty receptor for a painful vanilloid to a key player in hyperalgesia", *European Journal of Pharmacology*, vol. 500, pp. 231-241, Aug. 24, 2004.

(Continued)

*Primary Examiner* — Shailendra Kumar
(74) *Attorney, Agent, or Firm* — Rothwell, Figg, Ernst & Manbeck, P.C.

(57) ABSTRACT

This present invention relates to novel compounds, isomer thereof or pharmaceutically acceptable salts thereof as vanilloid receptor (Vanilloid Receptor 1; VR1; TRPV1) antagonist; and a pharmaceutical composition containing the same. The present invention provides a pharmaceutical composition for preventing or treating a disease such as pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, and heart disease.

9 Claims, No Drawings

OTHER PUBLICATIONS

Hwang, S. et al., "Hot channels in airways: pharmacology of the vanilloid receptor", *Current Opinion in Pharmacology*, vol. 2, pp. 235-242, 2002.

Geppetti, P. et al., "The transient receptor potential vanilloid 1: Role in airway inflammation and disease", *European Journal of Pharmacology*, vol. 533, pp. 207-214, Feb. 7, 2006.

Birder, L. et al., "Altered urinary bladder function in mice lacking the vanilloid receptor TRPV1", *Nature Neuroscience*, vol. 5, No. 9, pp. 856-860, Sep. 2002.

Birder, L. et al., "Vanilloid receptor expression suggests a sensory role for urinary bladder epithelial cells", *PNAS*, vol. 98, No. 23, pp. 13396-13401, Nov. 6, 2001.

Southall, M. et al., "Activation of Epidermal Vanilloid Receptor-1 Induces Release of Proinflammatory Mediators in Human Keratinocytes", *Journal of Pharmacology and Experimental Therapeutics*, vol. 304, No. 1, 217-222, Sep. 13, 2002.

Tominaga, M. et al., "The Cloned Capsaicin Receptor Integrates Multiple Pain-Producing Stimuli", *Neuron*, vol. 21, pp. 531-543, Sep. 1998.

Balaban, C. et al., "Type 1 vanilloid receptor expression by mammalian inner ear ganglion cells", *Hearing Research*, vol. 175, pp. 165-170, Oct. 21, 2002.

Scotland, R. et al., "Vanilloid Receptor TRPV1, Sensory C-Fibers, and Vascular Autoregulation: A Novel Mechanism Involved in Myogenic Constriction", *Circulation Research*, vol. 95, pp. 1027-1034, Oct. 12, 2004.

\* cited by examiner

COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

CROSS REFERENCE TO RELATED APPLICATION

This application is a 35 U.S.C. §371 National Phase Entry Application from PCT/KR2006/000988, filed Mar. 17, 2006, and designating the United States. This application claims priority under 35 U.S.C. §119 to Korean Patent Application No. 10-2005-0022986 filed Mar. 19, 2005 and claims benefit of U.S. Provisional Application Ser. No. 60/663,269 filed Mar. 21, 2005, which are incorporated herein in their entireties.

TECHNICAL FIELD

The present invention relates to novel compounds, isomer thereof or pharmaceutically acceptable salts thereof as vanilloid receptor (Vanilloid Receptor 1; VR1; TRPV1) antagonist; and a pharmaceutical composition containing the same.

BACKGROUND ART

As diseases associated with the activity of vanilloid receptor (Nagy et al., 2004, Eur. J. Pharmacol. 500, 351-369) pain such as acute pain, chronic pain, neuropathic pain, post-operative pain, rheumatic arthrodynia, osteoarthritis pain, postherpetic neuralgia, neuralgia, headache, and migraine (Petersen et al., 2000, Pain, 88, pp 125-133; Walker et al., 2003, J. Pharmacol. Exp. Ther., 304, pp 56-62); nerve-related diseases such as neuropathies, HIV-related neuropathy, nerve injury, neurodegeneration, and stroke (Park et al., 1999, Arch. Pharm. Res. 22, pp 432-434; Kim et al., 2005, J. Neurosci. 25(3), pp 662-671); diabetic neuropathy (Kamei et al., 2001, Eur. J. Pharmacol. 422, pp 83-86); fecal urgency; irritable bowel syndrome (Chan et al., 2003, Lancet, 361, pp 385-391); inflammatory bowel disease (Yiangou et al., 2001, Lancet, 357, pp 1338-1339); disease of digestive organ such as stomach-duodenal ulcer and Crohn's disease (Holzer P, 2004, Eur. J. Pharm. 500, pp 231-241; Geppetti et al., 2004, Br. J. Pharmacol., 141, pp 1313-1320); disease of respiratory organ such as asthma, chronic obstructive pulmonary disease (Hwang et al., 2002, Curr Opin Pharm pp 235-242; Spina et al., 2002, Curr Opin Pharm pp 264-272); urinary incontinence (Birder et al., 2002, Nat. Neuroscience, 5, pp 856-860); urinary bladder hypersensitiveness (Birder et al., 2001, Proc. Natl. Acad. Sci. 98, pp 13396-13401); neurotic/allergic/inflammatory skin disease such as psoriasis, pruritus and prurigo (Southall et al., 2003, J. Pharmacol. Exp. Ther., 304, pp 217-222); irritation of skin, eye or mucous membrane (Tominaga et al., 1998, Neuron 21 pp 531-543); hyperacusis; tinnitus; vestibular hypersensitiveness (Balaban et al., 2003, Hear Res. 175, pp 165-70); cardiac disease such as inotropic ischemia etc. (Scotland et al., 2004, Circ. Res. 95, pp 1027-1034; Pan et al., 2004, Circulation, 110, pp 1826-1831) can be enumerated.

The vanilloid receptor (VR1) is the receptor for capsaicin (8-methyl-N-vanillyl-6-nonenamide), a pungent ingredient in hot peppers. The molecular cloning thereof was also reported in 1997 (Caterina et al., 1997, Nature 389, pp 816-824). This receptor is a non-selective cation channel composed of 6 transmembrane domains and belongs to the TRP channel family. Recently, it was named TRPV1. On the other hand, it is known that the vanilloid receptor is activated by stimuli such as capsaicin, resiniferatoxin, heat, acids, anandamide, lipid metabolites or the like; thus it plays a crucial role as a molecular integrator of physico-chemically noxious stimuli in mammals (Tominaga et al., 1998, Neuron 21 pp 531-543; Hwang et al., 2000, PNAS, 97, pp 6155-6160). Activation of the vanilloid receptor by endogenous/exogenous stimuli leads to not only transmission of noxious stimuli, but also liberation of neuropeptides such as substance P, CGRP (Calcitonin Gene-Related Peptide) and the like, thereby causing neurogenic inflammation. The vanilloid receptor is highly expressed in primary afferent sensory neurons. It is also reportedly expressed in various organs and tissues such as the bladder, kidney, lungs, intestines and skin, and in the central nervous system (CNS) including the brain and non-neuronal tissues (Mezey et al., 2000, PNAS, 97, pp 3655-3660; Stander et al., 2004, Exp. Dermatol. 13, pp 129-139; Cortright et al., 2001, BBRC, 281, pp 1183-1189). In particular, TRPV1 receptor knock-out mice exhibit a normal response to harmful physical stimuli, but show a reduction in pain responses and sensory sensitivity to thermal stimuli by vanilloid, and exhibit little hyperalgesia to thermal stimuli even in an inflammatory state (Caterina et al., 2000, Science 288, pp 306-313; Davis et al., 2000, Nature 405, pp 183-187; Karai et al., 2004, J. Clin. Invest., 113, pp 1344-1352). Lately, an additional role of the vanilloid receptor is also anticipated by presentation of possibility that the vanilloid receptor may be present in the form of a heteromultimer with TRPV3, another TRP channel (Smith et al., 2002, Nature, 418, pp 186-190).

As mentioned above, the vanilloid receptor knock-out mice exhibited reduced responses to thermal or noxious stimuli, thus raising the possibility that vanilloid receptor antagonists may be utilized for prevention or treatment of various pain conditions. Recently, this possibility is supported by the report that the well-known vanilloid receptor antagonist, capsazepine also decreases hyperalgesia caused by physical stimuli in models of inflammatory and neuropathic pain (Walker et al., 2003, JPET, 304, pp 56-62; Garcia-Martinez et al., 2002, Proc. Natl. Acad. Sci. 99, 2374-2379). In addition, treatment of the primary culture of afferent nerve cells with the vanilloid receptor agonist, capsaicin etc., results in damage to nerve functions and furthermore death of nerve cells. The vanilloid receptor antagonist exerts defense actions against such damage to nerve functions and nerve cell death (Holzer P, 1991, Pharmacological Reviews, 43, pp 143-201; Mezey et al., 2000, PNAS, 97, 3655-3660). The vanilloid receptor is expressed in all regions of the gastrointestinal tract, for example, ganglia of tensor, tunica muscularis, mucosa and epithelial cells. In particular, the vanilloid receptor is highly expressed in inflammatory disorders of the colon and ileum.

In addition, activation of the vanilloid receptor stimulates sensory nerves, which in turn causes release of neuropeptides which are known to play a critical role in pathogenesis of bowel disorders. The role of the vanilloid receptor in development of gastrointestinal disorders is well elucidated and documented in recent scientific papers and journals, for example, Holzer P, 2004, Eur. J. Pharm. 500, pp 231-241; Geppetti et al., 2004, Br. J. Pharmacol., 141, pp 1313-1320. According to such references, it seems that the vanilloid receptor antagonists will be effective for prevention or treatment of gastrointestinal diseases such as gastro-esophageal reflux disease (GERD) and gastroduodenal ulcer (DU). It has been reported that the number of sensory nerves expressing the vanilloid receptor is increased in patients suffering from irritable bowel syndromes and such increased expression of the vanilloid receptor is known to be involved in the development of the disease (Chan et al., 2003, Lancet, 361, pp 385-391). Other investigations showed that expression of the vanilloid receptor is significantly increased in patients suffering from inflammatory bowel disorders. Taken together, it appears that the vanilloid receptor antagonist may also be therapeutically effective for such bowel disorders (Yiangou et al., 2001, Lancet, 357, pp 1338-1339). The vanilloid receptor-expressing afferent nerves are abundantly distributed in airway mucosa. Bronchial hypersensitivity is very similar to hyperalgesia, and protons and lipoxygenase products, known as endogenous ligands for the vanilloid receptor, are well known as crucial factors responsible for development of asthma and chronic obstructive pulmonary diseases (Hwang et al., 2002, Curr. Opin. Pharm. pp 235-242; Spina et al., 2002, Curr. Opin. Pharm. pp 264-272). Further, it has been reported that air-polluting substances, which are a kind of asthma-causing substances, i.e., particulate matter specifically acts on the vanilloid receptor and such action is inhibited by capsazepine, thus suggesting the possible applicability of vanilloid receptor antagonists to respiratory diseases (Veronesi et al., 2001, NeuroToxicology, 22, pp 795-810). Urinary bladder hypersensitiveness and urinary incontinence are caused by various central/peripheral nerve disorders or injury, and capsaicin-responsive sensory nerves play an important role in bladder function control and inflammation. In addition, immunoreactivity of the vanilloid receptor was reported in urinary bladder epithelium (urothelium) in rats and it was found that bladder overactivity induced by capsaicin was due to stimulation of vanilloid receptors present in nerve fibers, or various transmitters which are released by vanilloid receptors (Birder et al., 2001, Proc. Natl. Acad. Sci. 98, pp 13396-13401). Further, VR1 (TRPV1) −/− mice are anatomically normal, but exhibit non-excretory bladder contractions by low contractile force, as compared to normal mice, thus indicating that the vanilloid receptor affects functions of the bladder (Birder et al., 2002, Nat. Neuroscience, 5, pp 856-860). Some of vanilloid agonists are recently under development as therapeutics for treating bladder diseases. Vanilloid receptors are distributed in human epidermal keratinocytes as well as in primary afferent sensory nerves (Denda et al., 2001, Biochem. Biophys. Res. Commun., 285, pp 1250-1252; Inoue et al., 2002, Biochem. Biophys. Res. Commun., 291, pp 124-129), and are then involved in transmission of various noxious stimuli and pains such as skin irritation and pruritus, thereby having close correlation with etiology of dermatological diseases and disorders such as skin inflammation, due to neurogenic/non-neurogenic factors. This is supported by the report that the vanilloid receptor antagonist, capsazepine inhibits inflammatory factors in human skin cells (Southall et al., 2003, J. Pharmacol. Exp. Ther., 304, pp 217-222).

Based on the above-mentioned information, development of various vanilloid receptor antagonists is under way, and some patents and patent applications relating to vanilloid receptor antagonists under development were recently published, in which the above mentioned information is described well (Rami et al., 2004, Drug Discovery Today: Therapeutic Strategies, 1, pp 97-104).

As a result of extensive and intensive studies based on the theoretical background discussed above, the present inventors have synthesized novel compounds having antagonistic activity by selective action on a vanilloid receptor and thus completed the present invention. Surprisingly, it has been identified that compounds having either a dibenzyl urea structure with at least two substituent on one of the phenyl rings or a benzylcinnamoylamide structure with an either unbranched or more than onefold branched backbone are particularly active modulators of the vanilloid receptor.

Therefore, it is an object of the present invention to provide novel compounds useful as a potent antagonist for a vanilloid receptor, isomer thereof and pharmaceutically acceptable salts thereof; and a pharmaceutical composition comprising the same.

DISCLOSURE OF THE INVENTION

The present invention provides a novel compound of the formula (Ia), an isomer and/or a pharmaceutically acceptable salt thereof; and a pharmaceutical composition containing the same.

[Formula Ia]

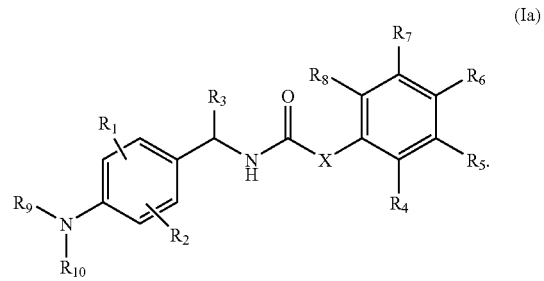

wherein,

X is $CR_{11}=CR_{12}$, or $C\equiv C$, wherein, $R_{11}$ and $R_{12}$ are independently hydrogen, halogen, C1-C5 alkyl, or phenyl;

$R_1$ and $R_2$ are independently hydrogen, carboxy, C1-C5 alkyl, halogen, nitro, C1-C5 alkoxy, halo (C1-C5) alkyl, C1-C5 alkylcarbonyl, C1-C5 alkylcarbonylamino, C1-C5 alkylsulfonylamino, phenylsulfonylamino, C1-C5 alkylthio, C1-C5 alkylsulfonyl, or C1-C5 alkoxycarbonyl;

$R_3$ is hydrogen, C1-C5 alkyl, C1-C5 alkoxy, or halo (C1-C5) alkyl;

$R_4$, $R_5$, $R_6$, $R_7$, and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkyl carbonyl, C1-C5 alkoxycarbonyl, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkyl carbonyl, C1-C5 alkylthio, C1-C5 alkylsulfonyl, or C1-C5 alkoxy carbonyl;

$R_9$ is C1-C5 alkylsulfonyl or C2-C5 alkenylsulfonyl; and $R_{10}$ is hydrogen;

provided that if $R_3$ is different from hydrogen, then $R_{11}$ and $R_{12}$ are not simultaneously hydrogen.

One preferred aspect of the present invention is a compound of the formula (Ia), an isomer thereof, and/or a pharmaceutically acceptable salt thereof;

wherein,

X is $CR_{11}=CR_{12}$ or $C\equiv C$, wherein, $R_{11}$ and $R_{12}$ are independently hydrogen, fluoro, bromo, chloro, iodo, methyl, ethyl, or propyl;

$R_1$ and $R_2$ are independently hydrogen, methyl, ethyl, propyl, fluoro, chloro, bromo, nitro, trifluoromethyl, methoxy, or ethoxy;

$R_3$ is hydrogen, methyl, ethyl, or methoxy;

$R_4$, $R_5$, $R_6$, $R_7$ and $R_8$ are independently hydrogen, carboxy, methyl, ethyl, propyl, isopropyl, butyl, t-butyl, sec-butyl, nitro, ethenyl, propenyl, methoxy, ethoxy, propoxy, C2-C5 alkynyl, trifloromethyl, methylthio, acetyl, methoxycarbonyl, phenyl, bromo, chloro, or Iodo, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, or C1-C5 alkoxycarbonyl;

$R_9$ is methanesulfonyl, ethanesulfonyl, or ethenylsulfonyl; and $R_{10}$ is hydrogen;

provided that if $R_3$ is different from hydrogen, then $R_1$, and $R_{12}$ are not simultaneously hydrogen.

Another preferred aspect of the present invention is a compound according to the above formula (Ia), an isomer, and/or a pharmaceutically acceptable salt thereof;

wherein,

X is trans $CR_{11}=CR_{12}$ or $C\equiv C$, wherein, $R_{11}$ and $R_{12}$ are independently hydrogen or methyl;

$R_1$ is hydrogen, methyl, ethyl, propyl, fluoro, chloro, bromo, iodo, nitro, methoxy, or ethoxy;

$R_2$ is hydrogen, methyl, fluoro, or chloro;

$R_3$ is hydrogen;

$R_4$, $R_5$, $R_7$, and $R_8$ are independently hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_6$ is halo (C1-C3) alkyl, isopropyl, or t-butyl;

$R_9$ is methanesulfonyl; and $R_{10}$ is hydrogen.

More preferred aspect of the present invention is a compound according to the formula (Ia), an isomer, and/or a pharmaceutically acceptable salt thereof;

wherein, X is trans $CR_{11}=CR_{12}$ or $C\equiv C$, wherein, $R_1$, and $R_{12}$ are independently hydrogen or methyl;

$R_1$ is hydrogen, methyl, ethyl, propyl, fluoro, chloro, bromo, or iodo;

$R_2$ is hydrogen, methyl, fluoro, or chloro;

$R_3$ is hydrogen;

$R_4$ is hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_5$, $R_7$ and $R_8$ are all hydrogen;

$R_6$ is isopropyl or t-butyl;

$R_9$ is methanesulfonyl; and $R_{10}$ is hydrogen.

Another preferred aspect of the present invention is a compound according to the formula (Ia), an isomer, and/or a pharmaceutically acceptable salt thereof;

wherein

X is $CR_{11}=CH$, $CH=CR_{12}$, $CR_{11}=CR_{12}$, or $C\equiv C$, wherein $R_{11}$ and $R_{12}$ are both methyl;

$R_1$ is hydrogen, methyl, ethyl, propyl, fluoro, chloro, bromo, iodo, nitro, methoxy or ethoxy;

$R_2$ is hydrogen, methyl, fluoro, or chloro;

$R_3$ is methyl;

$R_4$, $R_5$, $R_7$ and $R_8$ are independently hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_6$ is halo (C1-C3) alkyl, isopropyl, or t-butyl;

$R_9$ is methanesulfonyl; and $R_{10}$ is hydrogen.

More preferred aspect of the present invention is a compound according to the formula (Ia), an isomer, and/or a pharmaceutically acceptable salt thereof;

wherein X is $CR_{11}=CH$ or $C\equiv C$, wherein $R_{11}$ is methyl;

$R_1$ is hydrogen, methyl, ethyl, propyl, fluoro, chloro, bromo, or iodo;

$R_2$ is hydrogen, methyl, fluoro, or chloro;

$R_3$ is methyl;

$R_4$ is hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_5$, $R_7$ and $R_8$ are all hydrogen;

$R_6$ is isopropyl or t-butyl;

$R_9$ is methanesulfonyl; and $R_{10}$ is hydrogen.

Even more preferred aspect of the present invention is a compound according to the formula (Ia), an isomer, and/or a pharmaceutically acceptable salt thereof;

Wherein, $R_1$ is bound to the phenyl ring in ortho position to the sulfonyl amino group such that the compound has the formula (Ib).

[Formula Ib]

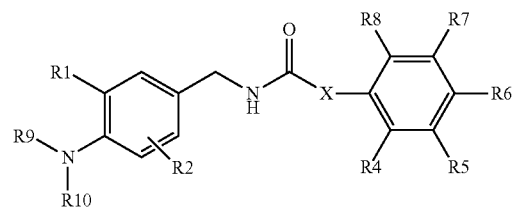

(Ib)

Preferred examples of compounds according to a compound of formula (Ia) are selected from the group consisting of;

3-(4-t-butyl-phenyl)-N-(4-methanesulfonylamino-benzyl)-2-methyl-acrylamide, 3-(4-t-butyl-phenyl)-N-(3-fluoro-5-iodo-4-methanesulfonylamino-benzyl)acrylamide, 3-(4-t-butyl-phenyl)-N-(4-methanesulfonylamino-benzyl)propiolicamide, (E)-3-(4-t-butyl-phenyl)-N-(3-fluoro-4-methanesulfonylamino-benzyl)acrylamide, 3-(4-t-butyl-phenyl)-N-(3-chloro-4-methanesulfonylamino-benzyl)acrylamide, 3-(4-t-butyl-phenyl)-N-(3-methyl-4-methanesulfonylamino-benzyl)acrylamide, 3-(4-t-butyl-phenyl)-N-(3,5-difluoro-4-methanesulfonylamino-benzyl)acrylamide, 3-(4-t-butyl-phenyl)-N-(2,5-difluoro-4-methanesulfonylamino-benzyl)acrylamide, 3-(4-t-butyl-phenyl)-N-(3-chloro-5-iodo-4-methanesulfonylamino-benzyl)acrylamide, 3-(4-t-butyl-phenyl)-N-(3-chloro-4-methanesulfonylamino-5-methyl-benzyl)acrylamide, 3-(4-t-butyl-phenyl)-N-(3-fluoro-4-methanesulfonylamino-5-methyl-benzyl)acrylamide, 3-(4-t-butyl-phenyl)-N-(3-fluoro-4-methanesulfonylamino-benzyl)-2-methyl-acrylamide, 3-(4-t-butyl-phenyl)-but-2-enoic acid 3-fluoro-4-methanesulfonylamino-benzylamide, 3-(4-t-butyl-phenyl)-N-[1-(R)-(4-methanesulfonylaminophenyl)ethyl]propiolicamide, 3-(4-t-butylphenyl)-N-[1-(R)-(4-methanesulfonylaminophenyl)ethyl]-2-methylacrylamide, and 3-(4-t-butyl-phenyl)-N-[1-(3-fluoro-4-methanesulfonylami-nophenyl)ethyl]-2-methyl-acrylamide.

The present invention also provides a novel compound of the formula (II), an isomer and/or a pharmaceutically acceptable salt thereof; and a pharmaceutical composition containing the same.

[Formula II]

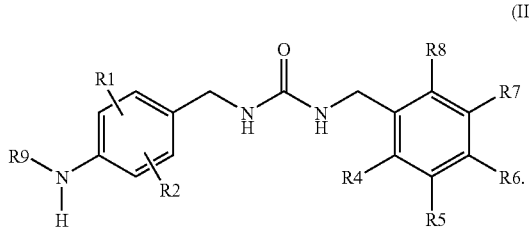

wherein, $R_1$ and $R_2$ are independently hydrogen, halogen, nitro, cyano, C1-C5 alkyl, C1-C5 alkoxy, halo (C1-C5) alkyl, carboxy, C1-C5 alkoxycarbonyl, or C1-C5 alkylthio, with the proviso that at least one of $R_1$ and $R_2$ is different from hydrogen;

$R_4$, $R_5$, $R_7$ and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkyl carbonyl, C1-C5 alkoxycarbonyl, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkyl carbonyl, C1-C5 alkylthio, C1-C5 alkylsulfonyl, or C1-C5 alkoxy carbonyl;

$R_6$ is halo(C1-C3) alkyl or C1-C5 alkyl; and $R_9$ is C1-C5 alkylsulfonyl, C2-C5 alkenylsulfonyl, or trifluoromethanesulfonyl.

One preferred aspect of the present invention is a compound of the formula (II), an isomer thereof, and/or a pharmaceutically acceptable salt thereof;

wherein, $R_1$ and $R_2$ are independently hydrogen, halogen, nitro, cyano, C1-C5 alkyl, C1-C5 alkoxy, halo (C1-C5) alkyl, carboxy, C1-C5 alkoxycarbonyl, or C1-C5 alkylthio, with the proviso that at least one of $R_1$ and $R_2$ is different from hydrogen;

$R_4$, $R_5$, $R_7$ and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkyl carbonyl, C1-C5 alkoxycarbonyl, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkyl carbonyl, C1-C5 alkylthio, C1-C5 alkylsulfonyl, or C1-C5 alkoxy carbonyl;

$R_6$ is C1-C5 alkyl; and $R_9$ is C1-C5 alkylsulfonyl, C2-C5 alkenylsulfonyl, or trifluoromethanesulfonyl.

More preferred aspect of the present invention is a compound according to the formula (II), an isomer, and/or a pharmaceutically acceptable salt thereof;

wherein, $R_1$ and $R_2$ are independently hydrogen, fluoro, chloro, bromo, iodo, nitro, cyano, methyl, ethyl, propyl, isopropyl, butyl, isobutyl, methoxy, ethoxy, trifluoromethyl, carboxy, or methoxycarbonyl, with the proviso that at least one of $R_1$ and $R_2$ is different from hydrogen;

$R_4$, $R_5$, $R_7$ and $R_8$ are independently hydrogen, carboxy, methyl, ethyl, propyl, isopropyl, t-butyl, nitro, ethenyl, ethynyl, isobutyl, methylthio, or methoxycarbonyl;

$R_6$ is C3-C5 alkyl; and $R_9$ is methanesulfonyl, ethanesulfonyl, or ethenesulfonyl.

Even more preferred aspect of the present invention is a compound according to the formula (II), an isomer, and/or a pharmaceutically acceptable salt thereof;

wherein, $R_1$ and $R_2$ are independently hydrogen, fluoro, chloro, bromo, iodo, nitro, cyano, methyl, ethyl, propyl, isopropyl, butyl, isobutyl, methoxy, ethoxy, trifluoromethyl, carboxy, or methoxycarbonyl; with the proviso that at least one of $R_1$ and $R_2$ is different from hydrogen;

$R_4$, $R_5$, $R_7$, and $R_8$ are hydrogen;

$R_6$ is isopropyl or t-butyl; and $R_9$ is methanesulfonyl.

Another preferred aspect of the present invention is a compound according to the formula (II), an isomer, and/or a pharmaceutically acceptable salt thereof;

wherein, $R_1$ is selected from fluoro, chloro, methyl, ethyl, n-propyl, or nitro;

$R_2$ is selected from fluoro, chloro, methyl, ethyl, or iodo, and $R_2$ may also be hydrogen when $R_1$ is selected from methyl, ethyl, or n-propyl;

$R_4$, $R_5$, $R_7$ and $R_8$ are independently hydrogen, halogen, carboxy, methyl, ethyl, propyl, isopropyl, t-butyl, nitro, ethenyl, ethynyl, isobutyl, methylthio, or methoxycarbonyl;

$R_6$ is halo(C1-C3) alkyl or C3-C5 alkyl; and $R_9$ is methanesulfonyl.

More preferred aspect of the present invention is a compound according to the formula (II), an isomer, and/or a pharmaceutically acceptable salt thereof;

wherein $R_1$ is bound to the phenyl ring in ortho position to the sulfonylamino group.

Even more preferred aspect of the present invention is a compound according to the formula (II), an isomer, and/or a pharmaceutically acceptable salt thereof;

wherein $R_1$ and $R_2$ are both bound in ortho position to the sulfonylamino group, such that the compound has the general formula (IIa)

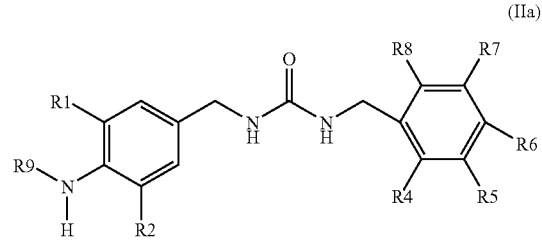

In the compounds of the formula (II) or (IIa) most preferably;

$R_1$ is methyl or ethyl and $R_2$ is selected from hydrogen, fluoro, or chloro.

Preferred examples of compounds according to a compound of formula (II) are selected from the group consisting of;

N-{4-[3-(4-t-butyl-benzyl)ureidomethyl]-2-fluoro-6-iodo-phenyl}methanesulfonamide, N-{4-[3-(4-t-butyl-benzyl)ureidomethyl]-5-chloro-2-iodo-phenyl}methanesulfonamide,
N-{4-[3-(4-t-butyl-benzyl)ureidomethyl]-2-ethyl-6-fluoro-phenyl}methanesulfonamide,
N-{4-[3-(4-t-butyl-benzyl)ureidomethyl]-2-fluoro-phenyl}methanesulfonamide,
N-{4-[3-(4-t-butyl-benzyl)ureidomethyl]-2-methyl-phenyl}methanesulfonamide,
N-{4-[3-(4-t-butyl-benzyl)ureidomethyl]-2-chloro-phenyl}methanesulfonamide,
N-{4-[3-(4-t-butyl-benzyl)ureidomethyl]-2-nitro-phenyl}methanesulfonamide,
N-{4-[3-(4-t-butyl-benzyl)-ureidomethyl]-2-iodo-phenyl}methanesulfonamide,
N-{4-[3-(4-t-butyl-benzyl)-ureidomethyl]-2,6-difluoro-phenyl}methanesulfonamide,
N-{4-[3-(4-t-butyl-benzyl)-ureidomethyl]-2,5-difluoro-phenyl}methanesulfonamide,
N-{4-[3-(4-t-butyl-benzyl)ureidomethyl]-2-chloro-6-methyl-phenyl}methanesulfonamide,
N-{4-[3-(4-t-butyl-benzyl)ureidomethyl]-5-chloro-2-ethyl-phenyl}methanesulfonamide, and
N-{4-[3-(4-t-butyl-benzyl)ureidomethyl]-2-fluoro-6-methyl-phenyl}methanesulfonamide.

The compounds of formula (Ia), (Ib), (II) or (IIa) according to the present invention can chemically be synthesized by the following reaction schemes. However, these are given only for illustration of the invention and not intended to limit them.

[Scheme 1]

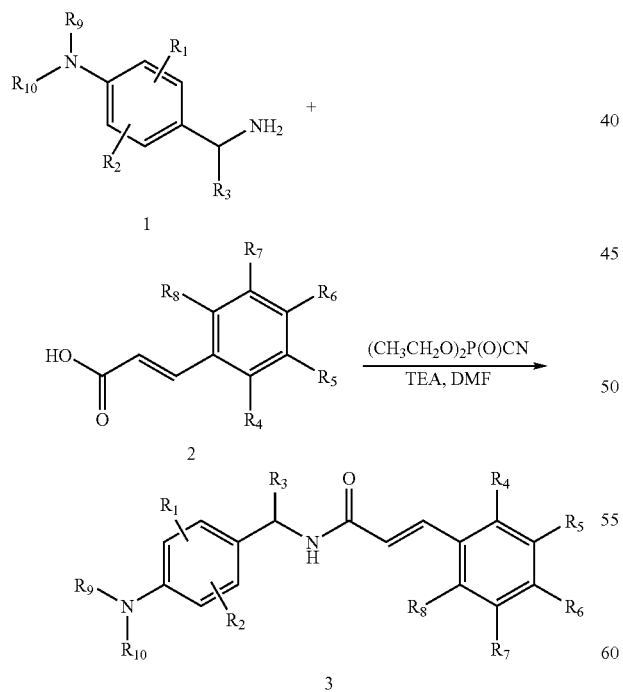

The above Scheme 1 shows a proposed process for synthesizing the acrylamide compounds (3). Unsaturated arylacrylic acid (2) was reacted with benzylamine and diethylcyanophosphate to yield acrylamide (3).

[Scheme 2]

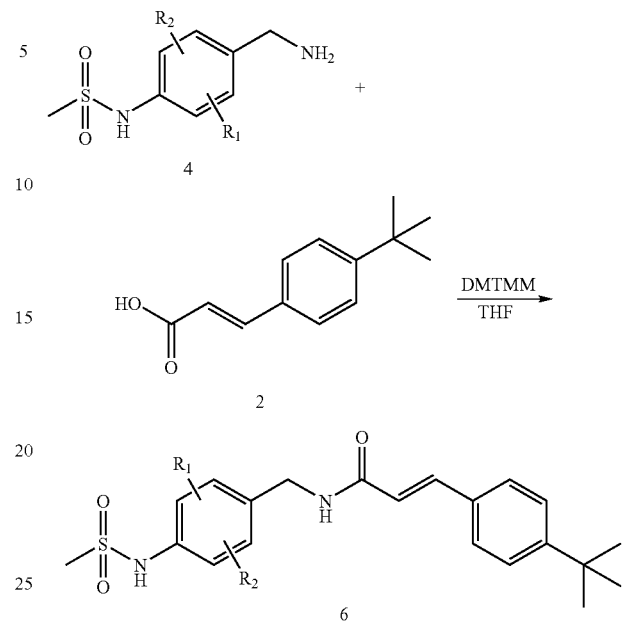

The Scheme 2 shows another process for synthesizing the acrylamide compound. The compound (6) is synthesized using DMTMM {4-(4,6-dimethoxy-1,3,5-triazin-2-yl)-4-methylmorpholinium chloride}(Tetrahedron Lett., 1999, 40, 5327) instead of diethylcyanophosphate.

[Scheme 3]

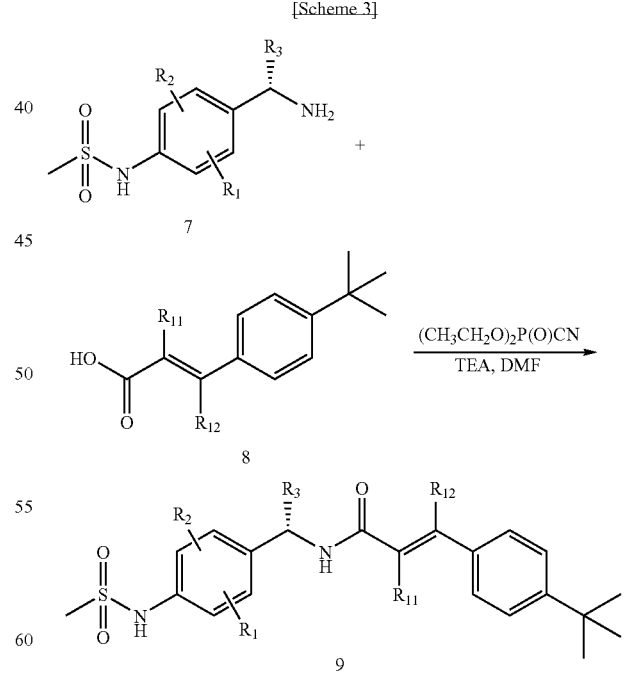

The Scheme 3 shows a proposed process for synthesizing the stereospecific acrylamide compounds (9). Arylacrylic acid (8) was reacted with benzylamine (7) to yield acrylamide (9) with structural variation on backbone.

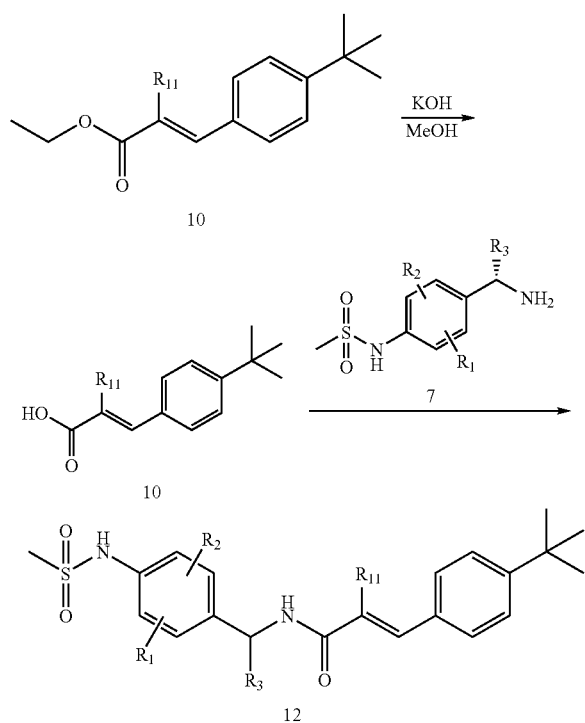

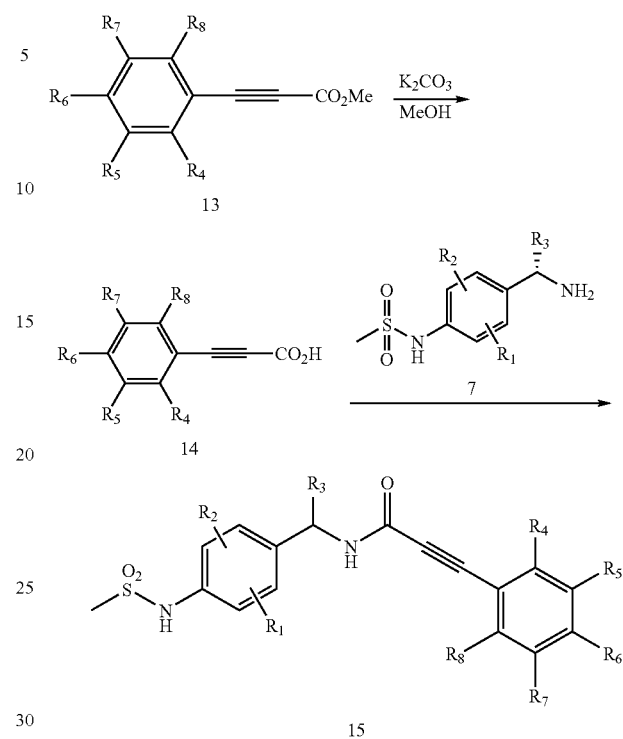

The Scheme 4 shows a proposed process for synthesizing the acrylamide derivatives (12). The ester compounds (10) having various substituents at alkene position of unsaturated fatty acid are hydrolyzed to yield the fatty acid (11). The compound (12) is synthesized using the unsaturated fatty acid (11) with substituent according to the same procedure as described in scheme 3.

The above Scheme 5 shows a proposed process for synthesizing the propiolic amide compound (15). The acid compound (14) possessing a triple bond is reacted with the benzylamine compound (7) to yield the purposed compound (15).

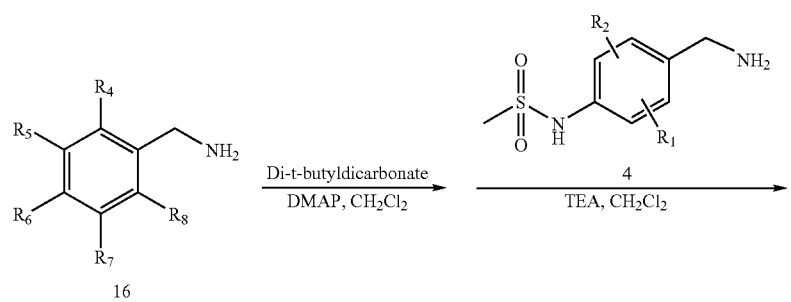

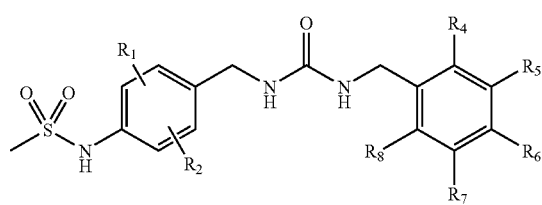

The above Scheme 6 shows a proposed process for synthesizing dibenzyl urea compounds (17). At first, substituted benzylamine is reacted with di-t-butyldicarbonate to yield benzyl carbamate in situ and to this reaction mixture is immediately added substituted benzylamine with methanesulfonyl group (4) and triethylamine to yield dibenzylurea compounds (17).

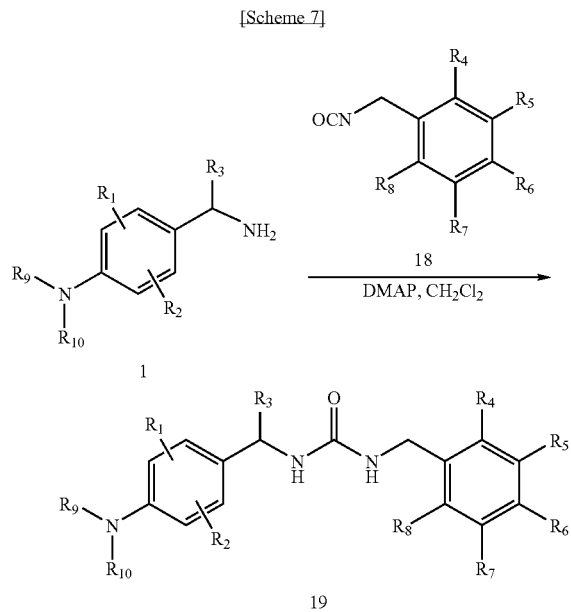

The above Scheme 7 shows a new process using benzyl isocyanate (18) to synthesize urea compounds (19).

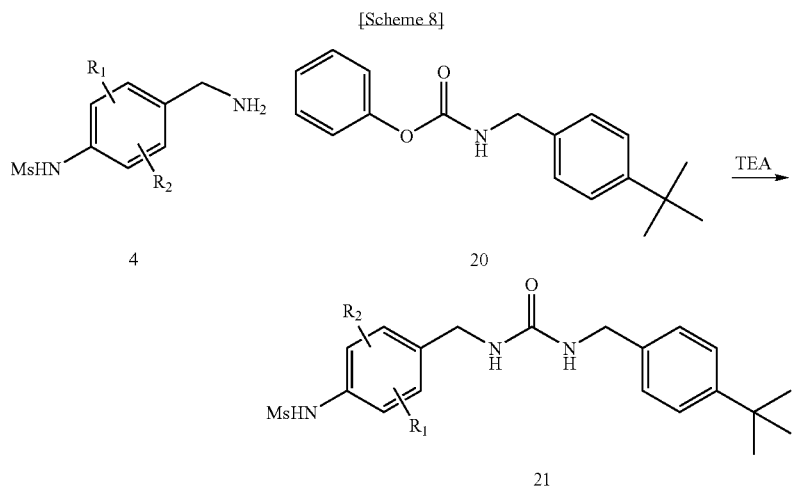

The Scheme 8 shows the other reaction for synthesizing various urea derivatives. Benzylamine compound with various substituents is reacted with (4-t-butyl-benzyl)-carbamic acid phenyl ester (20) to yield the urea compound (21).

The present invention also provides a pharmaceutical composition comprising a compound of formula (Ia), (Ib), (II) or (IIa), an isomer thereof, or a pharmaceutically acceptable salt thereof as an active ingredient together with a pharmaceutically acceptable carrier.

In said pharmaceutical composition, a compound of formula (Ia), (Ib), (II) or (IIa), an isomer thereof, or a pharmaceutically acceptable salt thereof as an active ingredient together with an pharmaceutically acceptable carrier is present in an effective amount for preventing or treating pain, acute pain, neuropathic pain, post-operative pain, migraine, arthralgia, neuropathies, nerve injury, diabetic neuropathy, neurodegeneration, stroke, neurotic/allergic/inflammatory skin disease, psoriasis, pruritus, prurigo, urinary bladder hypersensitiveness, irritable bowel syndrome, fecal urgency, Crohn's disease, respiratory disorder such as asthma or chronic obstructive pulmonary disease, irritation of skin, eye or mucous membrane, stomach-duodenal ulcer, inflammatory bowel disease or inflammatory diseases.

The present invention also provides a pharmaceutical composition for preventing and treating a disease associated with the pathological stimulation and/or aberrant expression of vanilloid receptor, wherein said composition comprises a compound of formula (Ia), (Ib), (II) or (IIa), an isomer thereof or a pharmaceutically acceptable salt thereof; and pharmaceutically acceptable carrier.

The present invention also provides a pharmaceutical composition for preventing and treating a condition related to vanilloid receptor, where said composition comprises a compound of formula (Ia), (Ib), (II) or (IIa), an isomer thereof or a pharmaceutically acceptable salt thereof and pharmaceutically acceptable carrier.

In the above, said condition related to vanilloid receptor is pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, or heart disease.

More specifically, said condition related to vanilloid receptor is acute pain, chronic pain, neuropathic pain, post-operative pain, rheumatic arthrodynia, osteoarthritis pain, postherpetic neuralgia, diabetic neuropathy, HIV-related neuropathy, neurodegeneration, stroke, neuroticlallergic/inflammatory skin disease, psoriasis, pruritus, prurigo, asthma, chronic obstructive pulmonary disease, urinary incontinence, inflammatory bowel disease, hyperacusis, tinnitus, vestibular hypersensitiveness, or inotropic ischemia.

In one preferred aspect, the present invention provides a pharmaceutical composition for treating a condition selected from pain, inflammatory disease of the joints including inflammatory autoimmune diseases of the joints, urinary bladder hypersensitivity including urinary incontinence, stomach duodenal ulcer, irritable bowel syndrome (IBS), and inflammatory bowel disease (IBD), neurotic/allergic/inflammatory skin disease, psoriasis, asthma, chronic obstructive pulmonary disease (COPD), pruritus, or prurigo comprising a compound, an isomer thereof or a pharmaceutically acceptable salt thereof according to anyone of formula (Ia), (Ib), (II) or (IIa), as defined further above.

More specific, the inventive compounds can be used in a pharmaceutical composition for treating pain, wherein the pain is—or is associated with—a condition selected from osteoarthritis ("OA"), rheumatoid arthritis ("RA"), Ankylosing Spondylitis ("AS"), diabetic neuropathic pain, post-operative pain, non-inflammatory musculoskeletal pain (including fibromyalgia, myofascial pain syndrome and back pain), migraine and other types of headaches.

If the compounds of the present invention are said to be useful to treat pain associated with osteoarthritis, it shall not be excluded that this also comprises the treatment of other signs and symptoms of osteoarthritis. Besides reducing the pain associated with osteoarthritis, the pharmacological intervention of osteoarthritis may be aimed at maintaining the mobility and minimizing the disability of the joints.

The term "inflammatory disease of the joints" includes diseases that involve to a more or less degree inflammatory processes in the joints, e.g. in knees, fingers, hips etc. An example for such a disease is osteoarthritis. The term "inflammatory disease of the joints" does also include diseases or conditions which may involve autoimmune processes, such as e.g. rheumatoid arthritis or ankylosing spondylitis. The inventive treatment of "inflammatory diseases of the joints" is primarily aimed at treating pain associated with these conditions but may also aim at improving the function of the affected joints, either directly or indirectly, e.g. by reducing the pain associated with the movement of said joints.

One outcome of the administration of the compounds of the present invention to patients suffering from an inflammatory disease of the joints may thus be reducing the pain experienced by the subject suffering from said disease relative to the pain experienced by the subject immediately before the administration of the compounds or combinations of the present invention. Another outcome of said treatment may be preventing the re-occurrence of pain which has previously been reduced as a result of pharmaco- or other therapy. Another outcome of treatment may be decreasing the occurrence of and/or the severity of manifestations related to an inflammatory disease of the joints, including particularly osteoarthritis, rheumatoid arthritis ankylosing spondylitis. The treatment may suitably result in an improved functionality of the joints, such as decreased stiffness, improved mobility.

The term "osteoarthritis (OA)" as used herein typically includes diseases with a failure of a diarthrodial (movable, synovial-lined) joint. In idiopathic (primary) OA, the most common form of the disease, no predisposing factor is apparent. Secondary OA is attributable to an underlying cause. Pain and joint dysfunction are the cardinal symptoms of OA. The joint pain of OA is often described as a deep ache and is localized to the involved joint. Typically, the pain of OA is aggravated by joint use and relieved by rest, but, as the disease progresses, it may become persistent. Nocturnal pain, interfering with sleep, is seen particularly in advance OA of the hip and may be enervating. Stiffness of the involved joint on arising in the morning or after a period of inactivity may be prominent but usually lasts less than 20 minutes.

The term "RA" refers to Rheumatoid Arthritis. RA is a chronic inflammatory autoimmune disease that causes the immune system to attack the joints, and particularly the synovium in the joint. The synovium becomes inflamed and causes swelling and pain. Cardinal symptoms of RA are joint pain and stiffness but additional symptoms include muscle aches, anemia and fever. Diagnosis of RA can be confirmed by detecting an antibody in the blood called the "rheumatic (or "rheumatoid") factor" and/or by a blood sedimentation test. Other useful and common tests are the detection of the "antinuclear antibody" or the "C-reactive protein".

"AS" stands for Ankylosing Spondylitis, which is a chronic, progressive autoimmune disease characterized by arthritis, inflammation and eventual immobility of the joints, particularly the spinal joints. It causes pain and stiffness in the back (often in the morning hours) as a result of ongoing swelling and irritation of the spinal joints (vertebrae). Inflammation of the tendons and ligaments that connect and provide support to the vertebrae can lead to pain and tenderness in the ribs, shoulder blades, hips, thighs, shins, heels and along the bony points of the spines.

If the compounds according to the present invention are said to be of use in treating pain associated with an inflammatory autoimmune disease of the joints, this refers to the administration of the compounds or combinations of the compounds of the present invention to reduce at least one pain symptom experienced by a subject suffering from an inflammatory autoimmune disease of the joints including back pain, joint pain and muscle pain associated with RA or AS. Besides the pain relief, treatment of an inflammatory autoimmune disease of the joints may also include a decrease of the inflammation and/or swelling of the synovium and may help to improve the functionality (i.e. maintaining mobility, and minimizing disability) of the joints, in particular in patients suffering from RA or AS.

Treatment of "non-inflammatory musculoskeletal pain" refers to the administration of the compounds or combinations of the compounds of the present invention to reduce the pain experienced by a subject suffering from non-inflammatory musculoskeletal pain including back pain, fibromyalgia, and myofascial pain syndrome. One outcome of treatment may be reducing the pain experienced by the subject relative to the pain experienced by the subject immediately before the administration of the compounds or combinations of the present invention. Another outcome of treatment may be preventing reoccurrence of pain which has previously been reduced as a result of pharmacotherapy. Another outcome of treatment may be decreasing the occurrence of and/or the severity of manifestations related to non-inflammatory musculoskeletal pain including back pain, fibromyalgia, and myofascial pain syndrome. The treatment may suitably result in a reduction of increased muscle sensitivity characterized by pain evoked by a normally non-nociceptive stimulus (allodynia) or increased pain intensity evoked by nociceptive stimuli (hyperalgesia). Finally, the treatment of non-inflammatory musculoskeletal pain can also improve the associated symptoms of back pain, fibromyalgia, and myofascial pain syndrome.

The terms "fibromyalgia" or "FMS" relates to a syndrome that causes widespread pain and stiffness throughout the tissue that supports and moves bones and joints. Fibromyalgia can be diagnosed by the presence of excessive tenderness on applying pressure to at least 11 of 18 specific muscle-tendon sites.

"Myofascial pain syndrome" is a chronic non-degenerative, non-inflammatory musculoskeletal pain condition. Distinct areas within muscles or their delicate connective tissue coverings (fascia) become abnormally thickened or tight.

When the myofascial tissues tighten and lose their elasticity, neurotransmitter ability to send and receive messages between the brain and body is damaged. Symptoms include muscle stiffness and aching and sharp shooting pains or tingling and numbness in areas distant from the trigger point. Most commonly trigger points are in the neck, back, or buttocks.

"Back pain" is a common non-inflammatory musculoskeletal pain condition that may be either acute or chronic. It may be caused by a variety of diseases and disorders that affect the lumbar spine. Low back pain is often accompanied by sciatica, which is pain that involves the sciatic nerve and is felt in the lower back, the buttocks, and the backs of the thighs.

The compounds of the present invention are also useful for treating signs and symptoms of an overactive bladder such as urinary incontinence, more specific urinary urge incontinence, urinary stress incontinence, urinary urgency, nocturia and/or urinary frequency.

The pharmaceutical compositions according to the present invention are preferably adapted for oral administration. Alternatively, if skin diseases are to be treated the pharmaceutical composition containing the inventive compounds may be also formulated for topical or transcutaneous use.

In another aspect, the present invention relates to a method for inhibiting vanilloid ligand from binding to vanilloid receptor in a patient, comprising contacting cells expressing vanilloid receptor in the patient with a compound of formula (Ia), (Ib), (II) or (IIa), an isomer thereof, or a pharmaceutically acceptable salt thereof.

In another aspect, the present invention relates to a method for preventing or treating a disease selected from pain, migraine, arthralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, which comprises administering to a mammal including a person in need thereof a therapeutically effective amount of a compound of formula (Ia), (Ib), (II) or (IIa), an isomer thereof, or a pharmaceutically acceptable salt thereof.

In the above method, the disease is also selected from acute pain, chronic pain, neuropathic pain, post-operative pain, diabetic neuropathy, neurodegeneration, stroke, neurotic/allergic/inflammatory skin disease, psoriasis, pruritus, prurigo, asthma, chronic obstructive pulmonary disease, urinary incontinence or inflammatory bowel disease.

In one preferred aspect of the invention, the above method is treating pain that is or that is associated with a condition selected from osteoarthritis ("OA"), rheumatoid arthritis ("RA"), Ankylosing Spondylitis ("AS"), diabetic neuropathic pain, non-inflammatory musculoskeletal pain (including fibromyalgia, myofascial pain syndrome and back pain), post-operative pain, migraine and other types of headache.

In another aspect, the present invention relates to the use of a compound of formula (Ia), (Ib), (II) or (IIa), an isomer thereof, or a pharmaceutically acceptable salt thereof as an antagonist of vanilloid receptor.

In another aspect, the present invention relates to the use of a compound of formula (Ia), (Ib), (II) or (IIa), an isomer thereof, or a pharmaceutically acceptable salt thereof for prevention or treatment of a condition related to vanilloid receptor, which is more specifically associated with the aberrant expression and/or aberrant activation of a vanilloid receptor.

In another aspect, the present invention relates to the use of a compound of formula (Ia), (Ib), (II) or (IIa), an isomer thereof, or a pharmaceutically acceptable salt thereof, in preparation of a medicament for prevention or treatment of a condition related to vanilloid receptor.

In a preferred aspect, the present invention relates to the use of a compound of formula (Ia), (Ib), (II) or (IIa), an isomer thereof, or a pharmaceutically acceptable salt thereof in the preparation of a medicament for the prevention or the treatment of a condition that is selected from pain, inflammatory autoimmune disease of the joints, urinary bladder hypersensitivity including urinary incontinence, stomach duodenal ulcer, irritable bowel syndrome (IBS) and inflammatory bowel disease (IBD), neuroticlallergic/inflammatory skin disease, psoriasis, asthma, chronic obstructive pulmonary disease (COPD), pruritus, or prurigo.

In a particularly preferred aspect, the present invention relates to the use of a compound for treating pain as described above, wherein the pain is or is associated with a condition that is selected from osteoarthritis ("OA"), rheumatoid arthritis ("RA"), Ankylosing Spondylitis ("AS"), diabetic neuropathic pain, post-operative pain, non-inflammatory musculoskeletal pain (including fibromyalgia, myofascial pain syndrome and back pain), migraine and other types of headaches.

Hereinafter, the formulating methods and kinds of excipients will be described, but the present invention is not limited to them.

A compound of formula (Ia), (Ib), (II) or (IIa), an isomer thereof or a pharmaceutically acceptable salt thereof according to the present invention can be prepared as a pharmaceutical composition containing pharmaceutically acceptable carriers, adjuvants, diluents and the like. For instance, the compounds of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointment or cream.

The compound according to the present invention may also be used in the forms of pharmaceutically acceptable salts thereof, and may be used either alone or in combination or in admixture with other pharmaceutically active compounds.

The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

The preferable dose level of the compounds according to the present invention depends upon a variety of factors including the condition and body weight of the patient, severity of the particular disease, dosage form, and route and period of administration, but may appropriately be chosen by those skilled in the art. The compounds of the present invention are preferably administered in an amount ranging from 0.001 to 100 mg/kg of body weight per day, and more preferably from 0.01 to 30 mg/kg of body weight per day. Doses may be administered once a day, or several times a day with each divided portions. The compounds of the present invention are used in a pharmaceutical composition in an amount of 0.0001~10% by weight, and preferably 0.001~1% by weight, based on the total amount of the composition.

The pharmaceutical composition of the present invention can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

DETAILED DESCRIPTION OF THE INVENTION
DEFINITIONS

When describing the compounds, pharmaceutical compositions containing such compounds, methods of using such compounds and compositions, and use of such compounds and compositions, all terms used in the present application shall have the meaning usually employed by a relevant person skilled in the art, e.g. by a medicinal chemists, pharmacist or physician. By the way of example some definitions of specific groups are given below:

"Alkyl" includes monovalent saturated aliphatic hydrocarbyl groups. The hydrocarbon chain may be either straight-chained or branched. This term is exemplified by groups such as methyl, ethyl, n-propyl, isopropyl, n-butyl, iso-butyl, t-butyl.

"Alkoxy" includes the group-OR where R is alkyl. Particular alkoxy groups include, by way of example, methoxy, ethoxy, n-propoxy, isopropoxy, n-butoxy, t-butoxy, sec-butoxy, n-pentoxy, 1,2-dimethylbutoxy, and the like.

"Alkenyl" includes monovalent olefinically unsaturated hydrocarbyl groups being straight-chained or branched and having at least 1 double bond. Particular alkenyl groups include ethenyl (—CH=CH$_2$), n-propenyl (—CH$_2$CH=CH$_2$), isopropenyl (C(CH$_3$)=CH$_2$), and the like. A preferred "alkenyl" group is ethenyl (vinyl).

"Alkynyl" includes acetylenically unsaturated hydrocarbyl groups being straight-chained or branched and having at least 1 triple bond. A preferred alkynyl group is ethynyl (acetylene).

"Alkylsulfonyl" includes a radical-S(O)$_2$R where R is an alkyl group as defined herein. Representative examples include, but are not limited to, methanesulfonyl, ethylsulfonyl, propylsulfonyl, butylsulfonyl and the like.

"Alkylthio" includes a radical-S—R where R is an alkyl group as defined herein that may be optionally substituted as defined herein. Representative examples include, but are not limited to, methylthio, ethylthio, propylthio, butylthio, and the like.

"Amino" refers to the radical-NH$_2$.

"Carboxy" refers to the radical —C(=O)OH.

"Ethenyl" refers to —CH=CH$_s$ which in the present application is also designated "vinyl".

"Ethynyl" refers to —C≡CH.

"Halo" or "halogen" refers to fluoro, chloro, bromo and iodo. Preferred halo groups are either fluoro or chloro.

"Haloalkyl" includes an "alkyl" group as defined further above which is substituted with one or more halogens which may be the same, e.g. in trifluoromethyl or pentafluoroethyl, or which may be different.

"Hydroxy" refers to the radical-OH.

"Nitro" refers to the radical-NO$_2$.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

"Pharmaceutically acceptable carrier" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

MODE FOR CARRYING OUT INVENTION

The present invention is more specifically explained by following examples and expirical examples. However, it should be understood that the extent of the present invention is not limited to the following examples and expirical examples

EXAMPLE 1

3-[4-t-butyl-phenyl]-N-[3-fluoro-4-methanesulfonylamino-benzyl]acrylamide

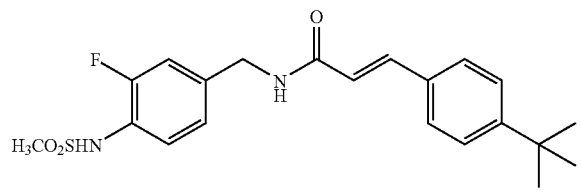

Step 1: 2-fluoro-4-iodo-1-methanesulfonylamino benzene

2-Fluoro-4-iodoaniline (1.50 g 6.33 mmol), pyridine (1.02 mL) and MsCl (700 μl, 9.50 mmol) were added in CH$_2$Cl$_2$ (40 mL). The reaction mixture was stirred at room temperature for 1 hour. The reaction was completed with 1.5N HCl. The resulting solution was extracted with CH$_2$Cl$_2$, dried over anhydride MgSO$_4$ and the remaining liquid was concentrated under reduced pressure. The residue was purified with column chromatography (n-hexane/ethyl acetate=1/1) to yield the compound 37a (1.89 g, 95%).

$^1$H-NMR (300 MHz, CDCl$_3$): δ 3.01 (s, 3H), 6.51 (s, 1H), 7.30 (t, 1H, J=8.3 Hz), 7.47 (dd, 2H, J=1.2, 1.7 Hz)

Step 2: 4-cyano-2-fluoro-1-methanesulfonylaminobenzene 2-fluoro-4-iodo-1-methanesulfonylamino benzene was dissolved in DMF (10 mL). Zn(CN)$_2$ (845 mg, 7.2 mmol) and Pd(PPh$_3$)$_4$ (187 mg, 0.16 mmol) were added into mixture. The reaction mixture was stirred at 80-90° C. for 1 hour and 30 minutes. The reaction solution was diluted with ethylacetate (20 mL). The mixture was washed with water and brine, dried over anhydride MgSO$_4$ and the remaining liquid was concentrated under reduced pressure. The residue was purified with column chromatography (n-hexane/ethyl acetate=2/1) to yield the compound 38a (1.03 g, 80%).

$^1$H-NMR (300 MHz, CDCl$_3$): δ 3.07 (s, 3H), 6.83 (s, 1H), 7.37 (dd, 1H, J=9.5, 1.7 Hz), 7.41 (d, 1H, J=9.8 Hz), 7.65 (t, 1H, J=8.0 Hz)

Step 3: 3-fluoro-4-methanesulfonylaminobenzylamine hydrochloride 4-cyano-2-fluoro-1-methanesulfonylaminobenzene (1.03 g) prepared in step 2 was dissolved in methanol (20 mL) and added a catalytic amount of 10 wt. % Pd/C and concentrated HCl (3 mL) to hydrogenate. The reaction solution was stirred at room temperature for 1 hour. The resulting solution was diluted with ether, filtered through celite, concentrated under reduced pressure and washed with ethylacetate to yield the title compound (1.13 g, 92%).

$^1$H NMR (300 MHz, CD$_3$OD): δ 3.02 (s, 3H), 4.11 (s, 2H), 7.27 (d, 1H, J=8.5 Hz), 7.33 (dd, 1H, J=9.8, 1.8 Hz), 7.57 (t, 1H, J=8.3 Hz)

Step 4: 3-[4-t-butyl-phenyl]-N-[3-fluoro-4-methanesulfonylamino-benzyl]acrylamide 3-[4-(t-Butyl)phenyl]-2-propenoic acid (500 mg, 2.45 mmol) and oxalyl chloride (2.0 eq, 0.43 mL, 4.89 mmol) were added in methylene chloride (10 mL). DMF (5 drops) was added into the mixture. The reaction mixture was stirred for 2 hrs. The reaction mixture was concentrated in vacuo. A residue and 3-fluoro-4-methanesulfonylamine HCl salt (1.2 eq, 748 mg, 2.94 mmol) were dissolved in methylene chloride (10 mL). Et$_3$N (2.4 eq, 0.82 mL, 5.87 mmol) was added into the mixture. The mixture was stirred for 2 hrs. The reaction mixture was purified with column chromatography (EtOAc: n-hexane=1:1) to yield 3-[4-t-butyl-phenyl]-N-[3-fluoro-4-methylsulfonylamino-benzyl]-2-propeneamide (264 mg, 27%).

$^1$H-NMR (300 MHz, CDCl$_3$): δ 1.30 (s, 9H), 3.00 (s, 3H), 4.54 (d, 2H, J=6.2 Hz), 5.93 (bs, 1H), 6.39 (d, 1H, J=15.6 Hz), 6.48 (bs, 1H), 7.15-7.09 (m, 2H), 7.39 (d, 2H, J=8.4 Hz), 7.45 (d, 2H, J=8.4 Hz), 7.54 (t, 1H, J=8.3 Hz), 7.66 (d, 1H, J=15.6 Hz)

EXAMPLE 2

3-(4-t-Butyl-phenyl)-N-(3-chloro-4-methanesulfonylamino-benzyl)-acrylamide

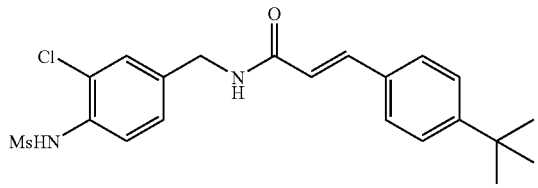

N-(4-Aminomethyl-2-chloro-phenyl)-methanesulfonamide, HCl salt (200 mg, 0.74 mmol) was reacted with 3-(4-t-butyl-phenyl)-acrylic acid following the general procedure to give a white solid (260 mg, 83%).

$^1$HNMR (300 MHz, CDCl$_3$): 7.68 (d, 1H, J=15.6 Hz), 7.61 (d, 1H, J=8.1 Hz), 7.43 (m, 5H), 7.26 (dd, 1H, J=2.1 and 8.1 Hz), 6.78 (bs, 1H), 6.40 (d, 1H, J=15.6 Hz), 6.03 (t, 1H, J=6.0 Hz), 4.54 (d, 2H, J=6.0 Hz), 3.00 (s, 3H), 1.33 (s, 9H).

EXAMPLE 3

3-(4-t-Butyl-phenyl)-N-(3-methyl-4-methanesulfonylamino-benzyl)-acrylamide

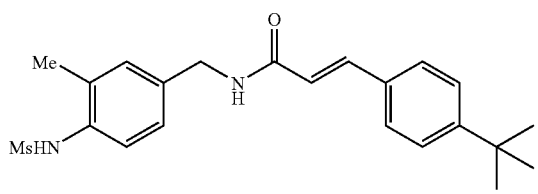

3-Methyl-4-methanesulfonylaminobenzylamine hydrochloride (140 mg, 0.56 mmol), 3-(4-t-butylphenyl)acrylic acid (1.1 eq, 0.13 g), and DMTMM (1.1 eq, 0.185 g) were added into 25 ml tetrahydrofuran. The reaction mixture was stirred 12 hours at room temperature. After confirming the completion of the reaction with TLC, the reaction mixture was extracted with ethylacetate, washed 1N HCl solution. And the combined organic layer was dried over MgSO$_4$, filtered and concentrated under reduced pressure. The obtained liquid was purified with column chromatography (n-hexane/ethyl acetate=2/1) to yield a solid (49 mg).

$^1$H NMR (300 MHz, CDCl$_3$): 7.65 (d, 1H, J=15.6 Hz), 7.42 (m, 4H), 7.19 (m, 2H), 6.37 (d, 1H, J=15.6 Hz), 6.17 (s, 1H), 5.88 (bs, 1H), 5.50 (bs, 1H), 4.53 (d, 2H, J=6.0 Hz), 3.02 (s, 3H), 2.32 (s, 3H), 1.32 (s, 9H).

EXAMPLE 4

3-(4-t-Butyl-phenyl)-N-(3,5-difluoro-4-methane-sulfonylamino-benzyl)-acrylamide

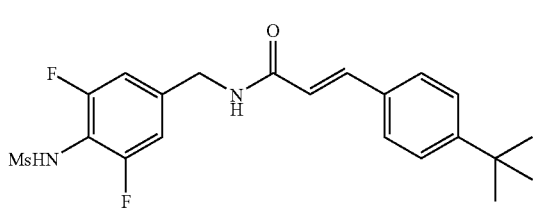

N-(4-Aminomethyl-2,6-difluoro-phenyl)-methanesulfonamide, HCl salt (100 mg, 0.37 mmol) was reacted with 3-(4-t-butyl-phenyl)-acrylic acid following the general procedure to give a white solid (150 mg, 96%).

$^1$H NMR (300 MHz, CDCl$_3$): 8.69 (t, 1H, J=6.0 Hz), 7.51 (d, 2H, J=8.4 Hz), 7.45 (d, 1H, J=15.6 Hz), 7.43 (d, 2H, J=8.4 Hz), 7.09 (d, 2H, J=8.4 Hz), 6.63 (d, 1H, J=15.6 Hz), 4.39 (d, 2H, J=6.0 Hz), 3.02 (s, 3H), 1.28 (s, 9H).

EXAMPLE 5

3-(4-t-Butyl-phenyl)-N-(2,5-difluoro-4-methane-sulfonylamino-benzyl)-acrylamide

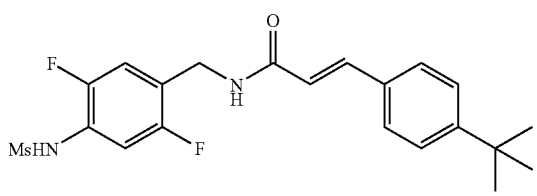

To the 25 ml round bottom flask were put N-(4-aminomethyl-2,5-difluoro-phenyl)-methanesulfonamide hydrochloride (125 mg, 0.46 mmol), 3-(4-t-butylphenyl)acrylic acid (1.2 eq, 112 mg), and DMTMM (1.2 eq, 152 mg). And to this mixture was poured 15 ml tetrahydrofuran and stirred 12 hours at room temperature. After confirming the completion of the reaction with TLC, the reaction mixture was extracted with ethylacetate, washed 1N HCl solution. And the combined organic layer was dried over MgSO$_4$, filtered and concentrated under reduced pressure. The obtained liquid was purified with column chromatography (n-hexane/ethyl acetate=1/1) to yield a solid (147 mg).

$^1$H NMR (300 MHz, CDCl$_3$): 7.65 (d, 1H, J=15.3 Hz), 7.35 (m, 5H), 6.75 (s, 1H), 6.39 (d, 1H, J=15.6 Hz), 6.15 (m, 1H), 4.54 (d, 2H, J=6.3 Hz), 3.04 (s, 3H), 1.32 (s, 9H).

EXAMPLE 6

3-(4-t-Butylphenyl)-N-(3-chloro-5-iodo-4-methane-sulfonylamino-benzyl)acrylamide

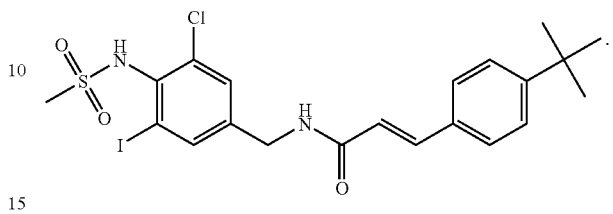

Step 1: 4-Amino-3-chloro-5-iodobenzonitrile

4-Amino-3-chloro-benzonitrile (100 mg, 0.66 mmol) and ICl (1.1 eq, 0.72 mmol, 117.05 mg) were added in methylene chloride. The reaction mixture was stirred for 12 hrs. The reaction mixture was quenched by adding sodium thiosulfate solution. Aqueous solution was extracted with methylene chloride. A combined organic solution was washed with H$_2$O and brine, dried with Na$_2$SO$_4$ and concentrated in vacuo. A residue was purified with column chromatography (n-Hx:EA=3:1) to yield 4-Amino-3-chloro-5-iodobenzonitrile (65.2 mg, 35.80%).

mp: 121~123° C.;
IR (KBr pellet, cm$^{-1}$): 3365, 2942, 2221, 1634, 728;
$^1$H NMR (400 MHz, CDCl$_3$): δ 7.42 (d, 1H, J=1.6 Hz), 7.43 (d, 1H, J=1.6 Hz), 5.01 (bs, 2H).

Step 2: (4-Amino-3-chloro-5-iodobenzyl)carbamic acid t-butyl ester

4-Amino-3-chloro-5-iodobenzonitrile (65.2 mg, 0.23 mmol) was dissolved in THF at 0° C. After Borane-THF complex (4 eq, 0.94 mmol, 0.94 ml) was slowly added into the reaction mixture. The reaction temperature was heated to reflux. The reaction mixture was stirred for 12 hrs with reflux. After confirming the completion of the reaction, MeOH was added. The mixture was stirred for 4 hrs. The reaction solvent was removed in vacuo. A residue was extracted with Ethyl acetate, washed with H$_2$O and brine, dried with Na$_2$SO$_4$ and concentrated in vacuo to yield 4-Aminomethyl-2-iodo-6-methyl-phenylamine (19.4 mg).

4-Aminomethyl-2-chloro-6-iodophenylamine (52.92 mg, 0.19 mmol) was dissolved in THF, and then BOC$_2$O (1.1 eq, 0.21 mmol, 47.48 ml) was slowly added. The reaction mixture was stirred for 12 hrs. A reaction mixture was extracted with Ethyl acetate, washed with H$_2$O and brine, dried with Na$_2$SO$_4$ and concentrated in vacuo. A residue was purified with column chromatography (n-Hx:EA=5:1) to obtain a solid (34.37 mg, 47.94%).

mp: 113~115° C.;
IR (KBr pellet, cm$^{-1}$): 3343, 1615, 717;
$^1$H NMR (400 MHz, CDCl$_3$): δ 7.39 (s, 1H), 7.09 (s, 1H), 4.76 (bs, 1H), 4.05 (bs, 2H), 4.05 (s, 2H), 1.38 (s, 9H)

Step 3: (3-Chloro-5-iodo-4-methanesulfonylaminobenzyl)carbamic acid t-butyl ester (4-Amino-3-chloro-5-iodobenzyl)carbamic acid t-butyl ester (254.7 mg, 0.67 mmol) was added into the methylene chloride under argon atmosphere. methanesulfonyl chloride (5 eq, 3.33 mmol, 258.04 µl) and TEA (3 eq, 2.00 mmol, 278.80 µl) were added into the mixture. The reaction mixture was stirred for 5 hrs. The reaction mixture was quenched by adding of aqueous NaHCO$_3$ soln. The mixture was extracted with methylene chloride. A combined organic layer was washed with CuSO$_4$, H$_2$O, and brine. The organic layer was dried Na$_2$SO$_4$, and then concentrated in vacuo. The residue was purified with column chromatography (THF:H2O=2:1) to yield compound. Compound and NaOH (5 eq, 3.33 mmol, 133.2 mg) were dissolved methanol. The reaction mixture was stirred for 12 hrs. The mixture was acidified with 10% HCl soln. The mixture was extracted with ethyl acetate. A combined organic layer was washed with H$_2$O and brine, dried with Na$_2$SO$_4$, and then concentrated in vacuo. The residue was purified with column chromatography (n-Hx:EA=3:1) to yield a yellow solid (122.0 mg, 39.78%).

Melting point: 139~141° C.; IR (KBr pellet, cm$^{-1}$): 3350, 2979, 1682, 1525, 1326, 769;
$^1$H NMR (400 MHz, CDCl$_3$): δ 7.66 (d, 1H, J=1.2 Hz), 7.31 (d, 1H, J=1.6 Hz), 7.25 (s, 1H), 4.88 (d, 1H, J=5.2 Hz), 4.18 (d, 2H, J=6.4 Hz), 3.24 (s, 3H), 1.40 (s, 9H).

Step 4: N-(4-Aminomethyl-2-chloro-6-iodo-phenyl)-methanesulfonamide (3-Iodo-4-methanesulfonylamino-5-methylbenzyl)carbamic acid t-butyl ester (122.0 mg, 0.27 mmol) and CF$_3$COOH (5~6 drops) were added into methylene chloride. The mixture was stirred for 12 hrs. The mixture was concentrated in vacuo to yield brownish syrup (142.2 mg, 100%).
$^1$H NMR (400 MHz, CD$_3$OD): 8.00 (d, 1H, J=2.0 Hz), 7.65 (d, 1H, J=1.6 Hz), 4.08 (s, 2H), 3.25 (s, 3H)

Step 5: 3-(4-t-Butylphenyl)-N-(3-chloro-5-iodo-4-methanesulfonylaminobenzyl)acrylamide N-(4-Aminomethyl-2-chloro-6-iodophenyl)methanesulfonamide (50 mg, 0.11 mmol) and 3-(4-t-butyl-phenyl)-acrylic acid (1.2 eq, 0.13 mmol, 25.84 mg) were added into DMF. DEPC (1.2 eq, 0.13 mmol, 19.72 µl) and TEA (2 eq, 0.22 mmol, 30.66 µl) were added into the mixture. The reaction mixture was stirred for 12 hrs. The reaction mixture was purified with column chromatography (n-Hx:EA=1:1) to yield white solid (33.4 mg, 55.61%).

Melting point: 173~175° C.; IR (KBr pellet, cm$^{-1}$): 3281, 2958, 1645, 1364, 760; $^1$H NMR (400 MHz, CD$_3$OD): δ 7.82 (d, 1H, J=2.0 Hz), 7.53 (d, 1H, J=15.6 Hz), 7.47 (d, 2H, J=8.4 Hz), 7.45 (d, 1H, J=2.0 Hz), 7.41 (d, 2H, J=8.4 Hz), 6.58 (d, 1H, J=16.0 Hz), 4.40 (s, 2H), 3.20 (s, 3H), 1.29 (s, 9H).

EXAMPLE 7

3-(4-t-Butyl-phenyl)-N-(3-chloro-4-methanesulfonylamino-5-methylbenzyl)acrylamide

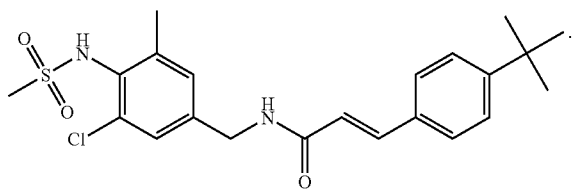

Step 1: 2-Chloro-4-iodo-6-methylphenylamine

2-Chloro-6-methyl-phenylamine (50 µl, 0.35 mmol) and ICl (1.1 eq, 0.39 mmol, 63.06 mg) were added into the methylene chloride. The mixture was stirred for 12 hrs. The mixture was quenched by adding of Sodium thiosulfate aqueous solution. The mixture was extracted with methylene chloride. A combined organic layer was purified column chromatography (n-Hx:EA=7:1) to yield a violet syrup (85.1 mg, 90%).
IR (NaCl neat, cm$^{-1}$): 3389, 3068, 2974, 760, 721;
$^1$H NMR (400 MHz, CDCl$_3$): δ 7.35 (d, 1H, J=1.6 Hz), 7.17 (m, 1H), 3.82 (bs, 2H), 2.07 (s, 3H).

Step 2: 4-Amino-3-chloro-5-methylbenzonitrile

2-Chloro-4-iodo-6-methyl-phenylamine (85.1 mg, 0.32 mmol) was dissolved in pyridine. CuCN (0.96 mmol, 85 mg) was added into the mixture. The mixture was stirred for 12 hrs in reflux. Reaction solvent was removed in vacuo. The residue was extracted with ethyl acetate. A combined organic layer was washed with brine, dried with Na$_2$SO$_4$, and then concentrated in vacuo. The residue was purified with column chromatography (n-Hx:EA=3:1) to obtain a solid (22.7 mg, 43%).
Melting point: 130~132° C.;
IR (KBr pellet, cm$^{-1}$): 3365, 2221, 728;
$^1$H NMR (400 MHz, CDCl$_3$): δ 7.36 (s, 1H), 7.15 (s, 1H), 4.46 (bs, 2H), 2.12 (s, 3H)

Step 3: (4-Amino-3-chloro-5-methylbenzyl)carbamic acid t-butyl ester

4-Amino-3-chloro-5-methyl-benzonitrile (499.4 mg, 3.00 mmol) and Borane-THF complex (4 eq, 12.04 mmol, 12.04 ml) were added in THF. The reaction mixture was stirred for 3 hrs in reflux. After confirming the completion of the reaction, MeOH was added slowly added in the mixture. MeOH was removed in vacuo. The residue was extracted with ethyl acetate. A combined organic layer was washed with H$_2$O and brine, dried with Na$_2$SO$_4$, concentrated in vacuo to yield 4-Aminomethyl-2-chloro-6-methyl-phenylamine (19.4 mg), as a yellow syrup.
4-Aminomethyl-2-chloro-6-methyl-phenylamine (571.5 mg, 3.36 mmol) and BOC$_2$O (0.8 eq, 2.69 mmol, 618.29 µl) were added into THF. The mixture was stirred for 12 hrs. After the reaction mixture was extracted with ethyl acetate, a combined organic layer was washed with H$_2$O and brine, dried with Na$_2$SO$_4$, and then concentrated in vacuo to obtain a solid (481.1 mg, 59%).
Melting point: 112~114° C.; IR (KBr pellet, cm$^{-1}$): 3370, 2964, 1696, 1623, 728;
$^1$H NMR (400 MHz, CDCl$_3$): δ 6.99 (s, 1H), 6.82 (s, 1H), 4.66 (bs, 1H), 4.08 (d, 2H, J=5.6 Hz), 2.11 (s, 3H), 1.38 (s, 9H).

Step 4: (3-Chloro-4-methanesulfonylamino-5-methylbenzyl)carbamic acid t-butyl ester (4-Amino-3-chloro-5-methylbenzyl)carbamic acid t-butyl ester (300 mg, 1.11 mmol), methanesulfonyl chloride (5 eq, 5.55 mmol, 428.81 µl) and TEA (3 eq, 3.33 mmol, 464.13 µl) were added into methylene chloride. The reaction mixture was stirred for 12 hrs. The reaction mixture was quenched by adding NaHCO$_3$ aqueous soln. The reaction mixture was extracted with methylene chloride. A mixture was purified with column chromatography (n-Hx:EA=3:1) to yield yellow solid (153.8 mg, 40%).

Melting point: 144~146° C.;

IR (KBr pellet, cm$^{-1}$): 3208, 2971, 1697, 1526, 1140, 758;

$^1$H NMR (400 MHz, CDCl$_3$): δ 7.13 (s, 1H), 7.01 (s, 1H), 6.75 (bs, 1H), 5.13 (bs, 1H), 4.16 (d, 2H, J=4.8 Hz), 3.02 (s, 3H), 2.39 (s, 3H), 1.40 (s, 9H).

Step 5: N-(4-Aminomethyl-2-chloro-6-methylphenyl)methanesulfonamide (3-Chloro-4-methanesulfonylamino-5-methyl-benzyl)-carbamic acid t-butyl ester (153.8 mg, 0.44 mmol) and CF$_3$COOH (5~6 drops) were added into methylene chloride. The mixture was stirred for 12 hrs. A reaction solvent was concentrated in vacuo to yield syrup (159.6 mg, 100%).

$^1$H NMR (400 MHz, CD$_3$OD): δ 7.44 (d, 1H, J=2.0 Hz), 7.30 (d, 1H, J=2.0 Hz), 4.04 (s, 2H), 3.09 (s, 3H), 2.44 (s, 3H).

Step 6: 3-(4-t-Butyl-phenyl)-N-(3-chloro-4-methanesulfonylamino-5-methylbenzyl)acrylamide N-(4-Aminomethyl-2-chloro-6-methylphenyl)methanesulfonamide (51.9 mg, 0.14 mmol) and 3-(4-t-butyl-phenyl)-acrylic acid (1.2 eq, 0.17 mmol, 35.11 mg) was added in DMF. DEPC (1.2 eq, 0.17 mmol, 25.49 μl) and TEA (2 eq, 0.28 mmol, 39.02 μl) was added into the mixture. The reaction mixture was stirred for 12 hrs. DMF was concentrated in vacuo. The residue was purified with column chromatography (n-Hx:EA=1:1) to yield white solid (59.6 mg, 98%).

Melting point: 153~155° C.;

IR (KBr pellet, cm$^{-1}$): 3240, 3065, 2963, 1656, 1320, 1152, 701;

$^1$H NMR (400 MHz, CDCl$_3$): δ 7.59 (d, 1H, J=15.6 Hz), 7.37 (d, 2H, J=8.4 Hz), 7.32 (d, 2H, J=8.4 Hz), 7.07 (s, 1H), 7.34 (d, 1H, J=15.6 Hz), 6.11 (s, 1H), 6.06 (t, 1H, J=5.6 Hz), 4.42 (d, 2H, J=5.6 Hz), 3.02 (s, 3H), 1.25 (s, 9H).

EXAMPLE 8

3-(4-t-butylphenyl)-N-(3-fluoro-5-iodo-4-methanesulfonylamino benzyl)acrylamide

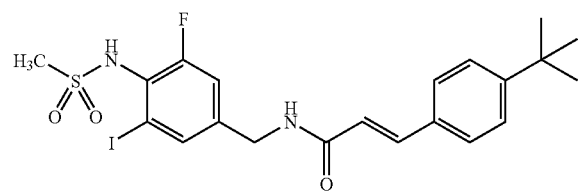

A 25 ml of two-neck round bottom flask was filled with argon gas and the solution of 3-(4-t-butyl-phenyl)-acrylic acid (59.4 mg, 0.291 mmol, 1 equiv.) and diethylcyanophosphine (48.6 μl, 0.320 mmol, 1.1 equiv.) in DMF was put into the flask. To the solution were added N-(4-aminomethyl-2-fluoro-6-iodophenyl)ethanesulfonamide (100 mg, 0.291 mmol, 1 equiv.) prepared in step 4 of Example 14 and triethylamine (121.7 μl, 0.873 mmol, 3 equiv.). The mixture was stirred for one night at room temperature. After confirming the completion of the reaction with TLC, the resulting solution was extracted with methylenechloride, washed with brine, dried over Na$_2$SO$_4$, filtered and concentrated under reduced pressure. The obtained solid was purified with column chromatography (n-hexane/ethyl acetate=1/1) to yield a yellow solid (59.8 mg, 38.7%).

mp: 139-140° C.

IR (KBr pellet, cm$^{-1}$): 3423, 3235, 2960, 2868, 1648;

$^1$H NMR (400 MHz, CD$_3$OD): 7.69 (s, 1H), 7.53 (d, 1H, J=15.6 Hz), 7.49 (d, 2H, J=8.4 Hz), 7.40 (d, 2H, J=8.4 Hz), 7.17 (dd, 1H, J=10.0, 1.6 Hz), 6.58 (d, 1H, J=15.6 Hz), 4.42 (s, 2H), 3.12 (s, 3H), 1.37 (s, 9H)

EXAMPLE 9

3-(4-t-Butyl-phenyl)-N-(3-fluoro-4-methanesulfonylamino-5-methyl-benzyl)-acrylamide

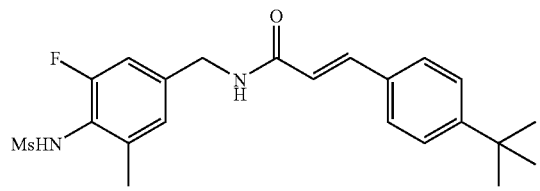

N-(4-Aminomethyl-2-fluoro-6-methyl-phenyl)-methanesulfonamide, and HCl salt (100 mg, 0.35 mmol) were reacted with 3-(4-t-butyl-phenyl)-acrylic acid following the general procedure to give a white solid (140 mg, 96%).

$^1$H NMR (300 MHz, CDCl$_3$): 7.64 (d, 1H, J=15.6 Hz), 7.41 (m, 4H), 7.25 (m, 2H), 6.35 (d, 1H, J=15.6 Hz), 6.18 (s, 1H), 5.94 (t, 1H), 4.58 (d, 2H, J=5.1 Hz), 3.03 (s, 3H), 2.24 (d, 2H, J=2.4 Hz), 1.32 (s, 9H).

EXAMPLE 10

3-(4-t-butylphenyl)-N-(4-methanesulfonylaminobenzyl)-2-methyl-acrylamide

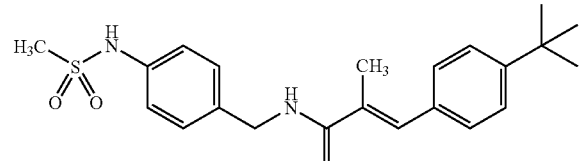

Step 1: the synthesis of 3-(4-t-butylphenyl)-2-methylacrylic acid ethyl ester

A 25 ml of two-neck round bottom flask was filled with argon gas and the solution of MgBr$_2$ diethyl etherate (1.2 eq, 95.51 mg, 0.37 mmol.) in tetrahydrofuran was put into the flask. TEA (1.54 eq, 0.48 mmol, 66.53 μl) and triethyl-2-phosphonopropionate (1.4 eq, 0.43 mmol, 94.50 μl) in tetrahydrofuran (1 ml) were added into the mixture. The reaction solution was stirred for 20 minutes. To the solution was added the solution of t-butyl benzaldehyde (50 μl, 0.31 mmol) in tetrahydrofuran (1 ml) slowly and stirred for 12 hours. After confirming the progress of the reaction with TLC, the reaction was quenched with NH$_4$Cl. The resulting solution was extracted with ethylacetate, washed with water and brine, dried over Na$_2$SO$_4$. The residue was purified with column chromatography (n-hexane/ethyl acetate=80/1) to yield an E-isomer 22.0 mg (crude-substrate and E-isomer mixture 32.1 mg) (29.00%).

IR (KBr pellet, cm$^{-1}$): 2963, 1707, 1634;
$^1$H NMR (400 MHz, CDCl$_3$): E-isomer NMR 7.59 (s, 1H), 7.35 (d, 2H, J=8.4 Hz), 7.28 (d, 2H, J=8.4 Hz), 4.19 (q, 2H, J=7.2 Hz), 2.06 (d, 3H, J=1.6 Hz), 1.27 (t, 3H, J=7.2 Hz), 1.26 (s, 9H).

Step 2: 3-(4-t-butylphenyl)-2-methylacrylic acid 3-(4-t-butyl-phenyl)-2-methyl-acrylic acid ethyl ester (516.3 mg, 2.10 mmol) was put into 25 ml of round-bottom flask and dissolved in a little of methanol. To the solution was added NaOH solution (3 eq, 6.29 mmol, 251.69 mg) slowly and stirred for 12 hours. After confirming the completion of the reaction with TLC, methanol was removed under reduced pressure. The resulting solution was acidified with 10% HCl to yield a white solid (411.5 mg, 89.94%).

mp: 130~132° C.;
IR (KBr pellet, cm$^{-1}$): 2959, 1671, 1267;
$^1$H NMR (400 MHz, CD$_3$OD): 7.64 (s, 1H), 7.42 (d, 2H, J=8.4 Hz), 7.34 (d, 2H, J=8.4 Hz), 2.06 (d, 3H, J=1.2 Hz), 1.30 (s, 9H).

Step 3: 3-(4-t-butylphenyl)-N-(4-methanesulfonylaminobenzyl)-2-methyl-acrylamide A dried 25 ml of two-neck round bottom flask was filled with argon gas and the solution of 3-(4-t-butyl-phenyl)-2-methyl-acrylic acid (200 mg, 0.92 mmol) and N-(4-aminomethyl-phenyl)-methanesulfonamide (1.2 eq, 1.10 mmol, 220.12 mg) in DMF was put into the flask. To the solution were added TEA (2 eq, 1.84 mmol, 256.46%) and diethylcyanophosphonate (1.2 eq, 1.10 mmol, 166.90 μl) and stirred for 12 hours. After confirming the completion of the reaction with TLC, DMF was removed under reduced pressure and extracted with ethylacetate. The ethylacetate layer was washed with water and brine, dried over Na$_2$SO$_4$, filtered and concentrated under reduced pressure. The obtained liquid was purified with column chromatography (n-hexane/ethyl acetate=2/1) to yield a white solid (124.0 mg, 33.80%).

mp: 133~135° C.;
IR (KBr pellet, cm$^1$): 3264, 2961, 1641, 1621, 1323;
$^1$H NMR (400 MHz, CDCl$_3$): 7.32 (d, 2H, J=8.0 Hz), 7.22 (d, 2H, J=8.0 Hz), 7.21 (d, 2H, J=8.0 Hz), 7.12 (d, 2H, J=8.0 Hz), 6.28 (t, 1H, J=5.6 Hz), 4.46 (d, 2H, J=5.6 Hz), 2.91 (s, 3H), 2.06 (s, 3H), 1.25 (s, 9H).

EXAMPLE 11

3-(4-t-Butylphenyl)-N-[1-(R)-(4-methanesulfonylaminophenyl)ethyl]-2-methylacrylamide

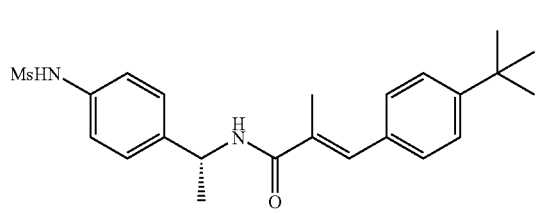

N-[4-(1-aminoethyl)phenyl]methanesulfonamide (0.25 mmol, 82.72 mg) and 3-(4-t-butylphenyl)-2-methylacrylic acid (0.23 mmol, 50 mg) were added in DMF. DEPC (0.27 mmol, 41.88%) and TEA (0.46 mmol, 64.11 μl) were added into the mixture. The mixture was stirred for 12 hrs. After DMF was removed in vacuo, the residue was extracted with ethyl acetate. A combined organic layer was washed with H$_2$O and brine, dried with Na$_2$SO$_4$, and then concentrated in vacuo. The residue was purified with column chromatography (n-Hx:EA-2:1→1:2) to yield a white solid (58.1 mg, 60.99%).

Melting point: 157~159° C.;
[a]$_D^{20}$–10.42 (CHCl$_3$, c 1.49);
IR (KBr pellet, cm$^{-1}$): 3266, 3015, 2962, 1615, 1322;
$^1$H NMR (400 MHz, CDCl$_3$): δ 7.57 (s, 1H), 7.36 (d, 2H, J=8.8 Hz), 7.31 (s, 1H), 7.27 (d, 2H, J=8.8 Hz), 7.25 (d, 2H, J=8.4 Hz), 7.16 (d, 2H, J=8.4 Hz), 6.25 (d, 1H, J=7.2 Hz), 5.16 (quin, 1H, J=7.2 Hz), 2.92 (s, 3H), 2.09 (s, 3H), 1.50 (d, 3H, J=7.2 Hz), 1.29 (s, 9H).

EXAMPLE 12

3-(4-t-Butylphenyl)-N-(3-fluoro-4-methanesulfonylaminobenzyl)-2-methylacrylamide

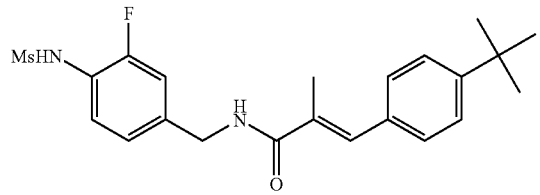

After N-(4-aminomethyl-2-fluorophenyl)methanesulfonamide (0.10 mmol, 30.0 mg) and 3-(4-t-butylphenyl)-2-methylacrylic acid (1.1 eq, 0.11 mmol, 21.68 mg) were dissolved in DMF, DEPC (1.2 eq, 0.12 mmol, 18.2 μl) and TEA (2 eq, 0.20 mmol, 27.88 μl) were added into mixture. The mixture was stirred for 12 hrs. DMF was removed in vacuo. The residue was purified with column chromatography (n-Hx:EtOAc=1:1) to yield a white solid (24.5 mg, 58.59%).

Melting point: 83~85° C.;
IR (KBr pellet, cm$^{-1}$): 3288, 3229, 3092, 2964, 1647, 1321, 1155; $^1$H NMR (400 MHz, CDCl$_3$): δ 7.45 (t, 1H, J=8.0 Hz), 7.37 (d, 2H, J=8.0 Hz), 7.35 (s, 1H), 7.24 (d, 2H, J=8.0 Hz), 7.11-7.06 (m, 2H), 6.85 (s, 1H), 6.45 (t, 1H, J=6.0 Hz), 4.49 (d, 2H, J=6.0 Hz), 2.97 (s, 3H), 2.11 (s, 3H), 1.30 (s, 9H).

EXAMPLE 13

3-(4-t-Butyl-phenyl)-but-2-enoic acid 3-fluoro-4-methanesulfonylamino-benzylamide

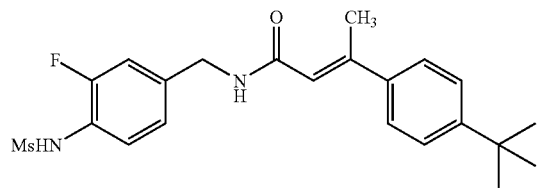

Step 1: 3-(4-t-butylphenyl)-but-2-enoic acid

The solution of ethyldiethylphosphonoacetate (1.2 eq, 0.25 g) in 4 ml of DMF was put into the flask and then cooled to 0°

C. To the solution was added 60% sodium hydride (1.4 eq, 1.27 mmol, 51 mg) and then added 4-t-butylphenylacetophenone (0.16 g, 0.91 mmol) in 3 ml DMF slowly. The mixture solution was stirred for 4 hours. After conforming the completion of the reaction with TLC, the reaction mixture was extracted with ethylacetate, and washed with water. The combined organic layer was dried over MgSO$_4$, filtered and concentrated under reduced pressure. The obtained liquid was dissolved in MeOH/THF solution and added 1N NaOH solution, and then refluxed overnight. After conforming the completion of the reaction with TLC, the reaction mixture was extracted with ethylacetate, and acidified with 1N HCl solution. And the combined organic layer was dried over MgSO$_4$, filtered and concentrated under reduced pressure. The obtained solid was purified with column chromatography to yield the title compound (134 mg, 68.1%)

Step 2: 3-(4-t-butyl-phenyl)-but-2-enoic acid-3-fluoro-4-methanesulfonylamino-benzylamide To the 50 ml of round bottom flask were put N-(4-aminomethyl-2-fluoro-phenyl)-methanesulfonamide hydrochloride (0.14 g, 0.55 mmol), 3-(4-t-butylphenyl)-but-2-enoic acid (1.0 eq, 0.12 g) and DMTMM (1.2 eq, 0.183 g). To this mixture was poured 25 ml tetrahydrofuran, added triethylamine (excess, 0.5 ml) and stirred 12 hours at room temperature. After confirming the completion of the reaction with TLC, the reaction mixture was extracted with ethylacetate, washed 1N HCl solution. The combined organic layer was dried over MgSO$_4$, filtered and concentrated under reduced pressure. The obtained liquid was purified with column chromatography (n-hexane/ethyl acetate=1/1) to yield the title compound (41.5 mg)

$^1$H NMR (300 MHz, CDCl$_3$): 7.53 (m, 1H), 7.39 (s, 4H), 7.14 (m, 2H), 6.48 (s, 1H), 6.03 (d, 1H, J=1.2 Hz), 5.93 (m, 1H), 4.50 (d, 2H, J=6 Hz), 3.02 (s, 3H), 1.32 (s, 3H).

EXAMPLE 14

3-(4-t-Butyl-phenyl)-N-[1-(3-fluoro-4-methanesulfonylaminophenyl)ethyl]-2-methylacrylamide

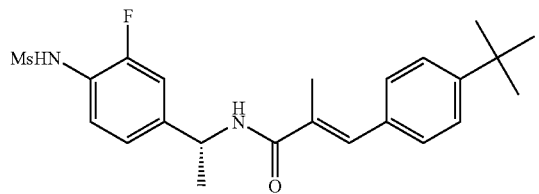

3-(4-t-Butyl-phenyl)-2-methylacrylic acid (1.1 eq, 0.14 mmol, 31.00 mg) and (R)-N-[4-(1-Amino-ethyl)-2-fluorophenyl]methanesulfonamide (1 eq, 0.13 mmol, 30 mg) were dissolved in DMF. DEPC (1.2 eq, 0.16 mmol, 23.67 μl) and TEA (2 eq, 0.26 mmol, 36.24 μl) were added into the mixture. The reaction mixture was stirred for 12 hrs. DMF was removed in vacuo. The residue was extracted with ethyl acetate and H$_2$O. A combined organic layer was washed with brine, dried with Na$_2$SO$_4$, and concentrated in vacuo. The residue was purified with column chromatography (n-Hx: EtOAc=1:1) to yield the title compound (52.53 mg, 93.5%) as a white solid.

Melting point: 92~94° C.;
[α]$_D^{20}$: −21.06 (CHCl$_3$, c 0.34);
IR (KBr pellet, cm$^{-1}$): 3335, 3249, 2964, 1615, 1509, 1325, 1163; $^1$H NMR (400 MHz, CDCl$_3$): δ 7.49 (t, 1H, J=8.0 Hz), 7.37 (d, 2H, J=8.0 Hz), 7.30 (s, 1H), 7.26 (d, 2H, J=8.0 Hz), 7.14 (s, 1H), 7.12 (d, 1H, J=3.6 Hz), 6.61 (s, 1H), 6.08 (d, 1H, J=7.6 Hz), 5.15 (qd, 1H, J=13.6, 6.8 Hz), 2.99 (s, 3H), 2.09 (s, 3H), 1.51 (d, 3H, J=6.8 Hz), 1.30 (s, 9H)

EXAMPLE 15

3-(4-t-butylphenyl)-N-[4-(methanesulfonylamino)benzyl]propiolicamide

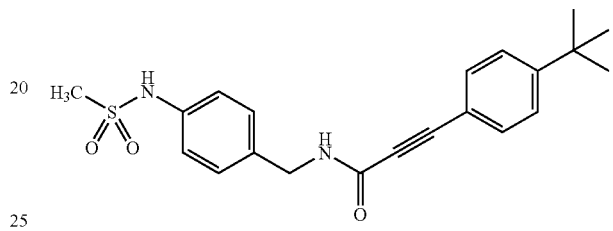

Step 1: (4-t-butyl-phenyl)-propionic acid methyl ester

A 100 ml of two-neck round bottom flask was filled with argon gas and the solution of 4-t-butyl-benzoyl chloride (500 mg, 2.34 mmol) in toluene was put into the flask. To the solution was added (triphenylphoshoranylidene)acetic acid methyl ester (1.5 eq, 3.52 mmol, 1178.39 mg) and refluxed for 12 hours at 90~100° C. After confirming the completion of the reaction with TLC, toluene was removed under reduced pressure and column-chromatographed (n-hexane/ethyl acetate=4/1) to yield a yellow solid (product 1).

A 50 of ml two-neck round bottom flask was filled with argon gas and the product (1) was put into the flask, heated and stirred for 90 minutes at 250° C. The reaction compound was extracted with methylenechloride and column-chromatographed (n-hexane/ethyl acetate=25/1) to yield a yellow liquid (product (2), 81.7 mg, 19.69%).

IR (KBr pellet, cm$^{-1}$): 2963, 2224, 1715, 1506, 1460;
$^1$H NMR (400 MHz, CDCl$_3$): product (1) 7.70~7.65 (m, 6H), 7.59 (d, 2H, J=8.4 Hz), 7.47~7.35 (m, 9H), 7.29 (d, 2H, J=8.8 Hz); product (2) 7.50 (d, 2H, J=8.0 Hz), 7.36 (d, 2H, J=5.0 Hz), 3.80 (s, 3H), 1.28 (s, 9H).

Step 2: (4-t-Butylphenyl)-propionic acid (4-t-butyl-phenyl)-propionic acid methyl ester (21.7 mg, 0.11 mmol) was put into 25 ml of round-bottom flask and dissolved in a little of methanol. To the solution was added K$_2$CO$_3$ solution slowly and stirred for 1 hour. After confirming the completion of the reaction with TLC, methanol was removed under reduced pressure and the residue was extracted with ethylacetate. The ethylacetate layer was washed with water and brine, dried over Na$_2$SO$_4$, filtered and then concentrated under reduced. The obtained liquid was purified with column chromatography (methanol:ethylacetate=1:1) to yield a white liquid (20.8 mg, 95.37%).

IR (KBr pellet, cm$^{-1}$): 3419, 2963, 2214, 1576, 1460;
$^1$H NMR (400 MHz, CDCl$_3$): 7.44 (d, 2H, J=8.8 Hz), 7.40 (d, 2H, J=8.4 Hz), 1.30 (s, 9H).

Step 3: 4-methanesulfonylaminobenzylamine hydrochloride 4-methanesulfonylaminobenzylcarbamic acid t-butyl ester (1.2 g, 4.0 mmol) was put into the 50 ml of one-neck round bottom flask and was poured with 30 ml of 1,4-dioxane. To the solution was added c-HCl (excess, 2 ml) and stirred for 4 hours. After confirming the completion of the reaction with TLC, the reaction solution was concentrated under reduced pressure. The obtained solid was washed with ethylacetate and filtered with glass filter. The obtained solid was dried in air to yield a solid (0.947 g, 100%).

$^1$H NMR (300 MHz, DMSO): 7.38 (d, 2H, J=8.4 Hz), 7.17 (d, 2H, J=8.4 Hz), 3.89 (s, 2H), 2.94 (s, 3H).

Step 4: 3-(4-t-butylphenyl)-N-[4-(methanesulfonylamino)benzyl]propiolicamide A dried 25 ml of two-neck round bottom flask was filled with argon gas and the solution of (4-t-butyl-phenyl)-propionic acid (24.5 mg, 0.12 mmol) prepared in step 2 and N-(4-aminomethyl-phenyl)-methanesulfonamide HCl (1.2 eq, 0.15 mmol, 29.10 mg) in DMF were put into the flask. To the solution were added TEA (2 eq, 0.24 mmol, 33.45 μl) and diethylcyano phosphonate (1.2 eq, 0.15 mmol, 24.46 μl), and stirred for 12 hours. After confirming the completion of the reaction with TLC, the resulting solution was extracted with ethylacetate, washed with water and brine, dried over Na$_2$SO$_4$, filtered and concentrated under reduced pressure. The obtained liquid was purified with column chromatography (n-hexane/ethyl acetate=1/1) to yield a white solid (10.1 mg, 21.68%).

mp: 128~130° C.
IR (KBr pellet, cm$^{-1}$): 3258, 2963, 2220, 1632, 1154;
$^1$H NMR (400 MHz, CDCl$_3$): 7.39 (d, 2H, J=8.4 Hz), 7.30 (d, 2H, J=8.0 Hz), 7.24 (d, 2H, J=8.4 Hz), 7.14 (d, 2H, J=8.0 Hz), 6.72 (s, 1H), 6.20 (t, 1H, J=5.2 Hz), 4.44 (d, 2H, J=6.0 Hz), 2.93 (s, 3H), 1.23 (s, 9H)

EXAMPLE 16

3-(4-t-butylphenyl)-N-[1-(R)-(4-methanesulfonylaminophenyl)ethyl]propiolicamide

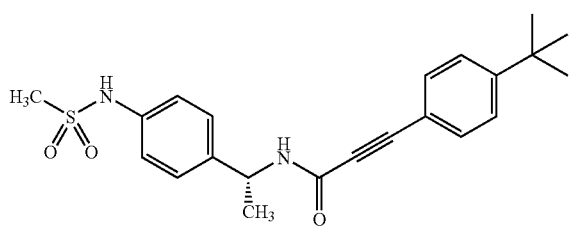

(4-t-butyl-phenyl)-propionic acid (92.58 mg, 0.46 mmol) and N-[4-(1-amino-ethyl)-phenyl]-methanesulfonamide (1.2 eq, 0.38 mmol, 124.1 mg) were added in DMF under argon atmosphere. TEA (2 eq, 0.76 mmol, 105.92 mg) and diethylcyanophosphonate (1.2 eq, 0.57 mmol, 86.48 μl) were added into the reaction mixture. The mixture was stirred for 12 hours. After confirming the completion of the reaction with TLC, the resulting solution was extracted with methylene chloride, washed with water and brine, dried over Na$_2$SO$_4$, filtered and concentrated under reduced pressure. The obtained liquid was purified with column-chromatography (n-hexane/ethyl acetate=211) to yield a white solid (112 mg, 61.40%).

mp: 95~97° C.;
$[\alpha]^{20}_D$:-32.33° C. (CHCl$_3$, c 0.18);
IR (KBr pellet, cm$^{-1}$): 3257, 3030, 2965, 2212, 1627, 1328;
$^1$HNMR (400 MHz, CDCl$_3$): δ 7.65 (bs, 1H), 7.40 (d, 2H, J=8.4 Hz), 7.32 (d, 2H, J=8.4 Hz), 7.25 (d, 2H, J=8.4 Hz), 7.17 (d, 2H, J=8.4 Hz), 6.57 (bs, 1H), 5.11 (quin, 1H, J=6.8 Hz), 2.92 (s, 3H), 1.46 (d, 3H, J=6.8 Hz), 1.25 (s, 9H).

EXAMPLE 17

N-{4-[3-(4-t-butylbenzyl)ureidomethyl]-2-fluoro-6-iodophenyl}methanesulfonamide

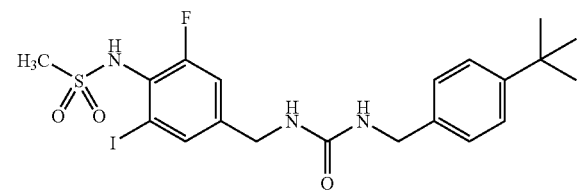

Step 1: 4-amino-3-fluorobenzonitrile

A 50 ml of two-neck round bottom flask was filled with argon gas, and the solution of 2-fluoro-4-iodoaniline (1 g, 5.219 mmol, 1 equiv.) in DMF was put into the flask. To the solution was added Copper (I) cyanide (453.4 mg, 5.063 mmol, 1.2 equiv.) and heated to reflux for 5 hours. After confirming the completion of the reaction with TLC, saturated sodium bicarbonate solution was added to the solution and stirred for 5 minutes. The resulting solution was extracted with methylenechloride, washed with water and brine, dried over Na$_2$SO$_4$, filtered and evaporated. The obtained liquid was column-chromatographed (n-hexane/ethyl acetate=2/1) to yield a pale yellow solid (461.6 mg).

$^1$H NMR (400 MHz, CDCl$_3$): 8.02 (d, 2H, J=8.8 Hz), 7.30 (d, 2H, J=8.8 Hz), 7.03 (d, 2H, J=8.4 Hz), 6.99 (d, 2H, J=8.4 Hz), 5.51 (bs, 1H), 4.90 (q, 1H, J=6.8 Hz), 2.44 (t, 2H, J=7.2 Hz), 1.50 (sextet, 2H, J=7.2 Hz), 1.26 (d, 3H, J=6.8 Hz), 0.84 (t, 3H, J=7.2 Hz)

Step 2: 4-amino-3-fluoro-5-iodobenzonitrile

A 25 ml of two-neck round bottom flask was filled with argon gas and the solution of 4-amino-3-fluoro-benzonitrile (300 mg, 2.204 mmol, 1 equiv.) in methylenechloride was put into the flask. To the solution was added iodomonochloride (393.6 mg, 2.424 mmol, 1.1 equiv.) and stirred for 1 hour. After confirming the completion of the reaction with TLC, to resulting solution was added saturated sodium thiosulphate solution and stirred. The reaction solution was extracted with methylenechloride, washed with water(twice) and brine, dried over Na$_2$SO$_4$, filtered and concentrated under reduced pressure. The obtained liquid was column-chromatographed (n-hexane/ethylacetate=3/1) to yield a brown liquid.

$^1$H NMR (400 MHz, CDCl$_3$): 7.64 (t, 1H, J=1.6 Hz), 7.32 (t, 0.3H, J=1.6 Hz), 7.18 (dd, 1H, J=10.4, 1.6 Hz), 7.15 (dd, 0.3H, J=10.4, 1.6 Hz), 4.63 (bs, 2H), 4.56 (bs, 0.6H)

Step 3: N-(4-cyano-2-fluoro-6-iodophenyl)methane-sulfonamide

A 25 ml of two-neck round bottom flask was filled with argon gas and the solution of 4-amino-3-fluoro-5-iodo-benzonitrile (1 g, 3.818 mmol, 1 equiv.) in methylenechloride was put into the flask and then cooled to 0° C. To the solution were added methanesulfonyl chloride (310.3 μl, 4.009 mmol, 1.05 equiv.) and triethylamine (1.06 ml, 7.636 mmol, 2 equiv.). The temperature of the mixture solution was raised to room temperature and heated to reflux for one night. After confirming the completion of the reaction with TLC, methylenechloride was removed under reduced pressure. To the solution were added the solution (THF:$H_2O$=2:1) and NaOH (763.6 mg, 19.090 mmol, 5 equiv.), and stirred for 10 minutes. The resulting solution was acidified by 10% HCl, extracted with ethylacetate, washed with brine, dried over $Na_2SO_4$, filtered and concentrated under reduced pressure. The obtained solid was column-chromatographed (n-hexane/ethylacetate=2/1) to yield an orange colored solid. (388.3 mg, substrate recovery 599 mg) (29.90% (74.57%)).

mp: 145~147° C.

IR (KBr pellet, $cm^{-1}$): 3432, 3212, 3088, 3019, 2937, 2237, 1317, 1145;

$^1$H NMR (400 MHz, $CD_3OD$): 8.09 (t, 1H, J=2.0 Hz), 7.66 (dd, 1H, J=9.6, 2.0 Hz), 3.15 (s, 3H)

Step 4: N-(4-aminomethyl-2-fluoro-6-iodophenyl)methanesulfonamide

A 50 ml of two-neck round bottom flask was filled with argon gas and the solution of 4-amino-3-fluoro-5-iodo-benzonitrile (330 mg, 0.970 mmol, 1 equiv.) in tetrahydrofuran was put into the flask and then cooled to 0° C. To the solution was added Borane-THF complex solution (1.0M, 1.94 ml, 1.941 mmol, 2 equiv.). The temperature of the mixture solution was raised to room temperature and heated to reflux. After confirming the completion of the reaction with TLC, the solution was cooled to 0° C. The reaction was quenched by adding methanol slowly. The resulting solution was extracted with ethylacetate, washed with brine, dried over $Na_2SO_4$. The obtained liquid was concentrated under reduced pressure to yield a yellow solid (237.5 mg, 71.14%).

mp: 124-126°;

IR (KBr pellet, $cm^{-1}$): 3439, 3239, 3069, 2927, 1610, 1323, 1152;

$^1$H NMR (400 MHz, $CD_3OD$): 7.80 (s, 1H), 7.30 (dd, 1H, J=10.0, 2.0 Hz), 3.96 (s, 2H), 3.14 (s, 3H)

Step 5: N-{4-[3-(4-t-butylbenzyl)ureidomethyl]-2-fluoro-6-iodophenyl}methanesulfonamide N-{4-[3-(4-t-butyl-benzyl)-ureidomethyl]-2-fluoro-6-iodo-phenyl}methanesulfonamide (Boc) (27 mg, 0.0426 mmol, 1 equiv.) was put into 25 ml of round-bottom flask and dissolved in methylenechloride. To the solution was added trifluoro acetic acid (3.6118 ul, 0.0469 mmol, 1.1 equiv.) and stirred for one night at room temperature. After confirming the completion of the reaction with TLC, the reaction solution was neutralized with sodium bicarbonate and confirmed with pH paper. The solution was extracted with methylenechloride, washed with brine, dried over $Na_2SO_4$ and concentrated under reduced pressure. The obtained liquid was column-chromatographed (n-hexane/ethylacetate=1/1) to yield a pale yellow solid (11 mg, 48.39%).

IR: 3408, 1634, 1567, 1321;

$^1$H NMR (400 MHz, $CD_3OD$) 1.30 (s, 9H), 3.15 (s, 3H), 4.30 (s, 2H), 7.36 (d, 1H, J=8.4 Hz), 7.20 (d, 1H, J=8.4 Hz), 7.69 (d, 1H, J=1.6 Hz), 7.15 (dd, 1H, J=1.6, 10.4 Hz)

EXAMPLE 18

N-{4-[3-(4-t-butylbenzyl)ureidomethyl]-5-chloro-2-Iodophenyl}methanesulfonamide

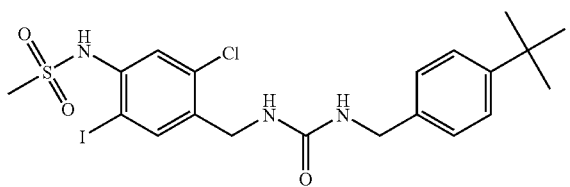

Step 1: 4-amino-2-chloro-5-iodobenzonitrile

A dried 25 ml of two-neck round bottom flask was filled with argon gas and the solution of 4-amino-2-chloro-benzonitrile (50 mg, 0.33 mmol) in methylenechloride was put into the flask. To the solution was added ICl (1.1 eq, 0.36 mmol, 58.52 mg) and stirred for 12 hours. After confirming the completion of the reaction with TLC, the reaction was quenched with $Na_2S_2O_3$. The reaction solution was extracted with methylenechloride, washed with water and brine, dried over $Na_2SO_4$, filtered and concentrated under reduced pressure. The obtained liquid was column-chromatographed (n-hexane/ethylacetate=3/1) to yield a white solid (27.5 mg, substrate recovery-9.6 mg, Crude-7.7 mg). (30.20%).

mp: 158~160° C.

IR (KBr pellet, $cm^{-1}$): 3350, 2922, 2218, 799;

$^1$H NMR (400 MHz, $CDCl_3$): 7.78 (s, 1H). 6.75 (s, 1H), 4.67 (bs, 2H)

Step 2: 4-aminomethyl-5-chloro-2-iodophenylamine

A dried 25 ml of two-neck round bottom flask was filled with argon gas. The solution of 4-amino-2-chloro-5-iodo-benzonitrile (63.8 mg, 0.23 mmol) in tetrahydrofuran was put into the flask and cooled to 0° C. To the solution was added Borane-THF complex (2 eq, 0.46 mmol, 0.4 ml) slowly. The temperature of the mixture was raised and heated to reflux for 12 hours. After confirming the completion of the reaction with TLC, to the solution was added methanol slowly (generation of bubbles) and stirred for 2 hours. The methanol was removed under reduced pressure and the residue was extracted with ethylacetate. The ethylacetate layer was washed with water and brine, dried over $Na_2SO_4$, filtered, and concentrated under reduced pressure to yield a yellow syrup (46.5 mg, 71.85%).

$^1$H NMR (400 MHz, $CD_3OD$): 7.56 (s, 1H), 6.72 (s, 1H), 3.72 (s, 2H)

Step 3: (4-amino-2-chloro-5-iodobenzyl)carbamic acid t-butyl ester

A dried 25 ml of two-neck round bottom flask was filled with argon gas and the solution of 4-aminomethyl-5-chloro-2-iodo-phenylamine (445.1 mg, 1.58 mmol) in tetrahydrofuran was put into the flask. To the solution was added Boc₂O (1.2 eq, 1.89 mmol, 435.68 ml) slowly and stirred for 12 hours. After confirming the completion of the reaction with TLC, the reaction solution was extracted with ethylacetate, washed with water and brine, dried over Na₂SO₄, filtered and concentrated under reduced pressure. The obtained liquid was purified with column chromatography (n-hexane/ethyl acetate=5/1) to yield a white solid (502.9 mg, 83.39%).

mp: 117~119° C.;

IR (KBr pellet, cm⁻¹): 3325, 2974, 1683, 1251, 755; 1 HNMR (400 MHz, CDCl₃): 7.52 (s, 1H), 6.65 (s, 1H), 4.82 (bs, 1H), 4.17 (d, 2H, J=4.8 Hz), 4.05 (bs, 2H), 1.38 (s, 9H)

Step 4: (2-chloro-5-Iodo-4-methanesulfonylaminobenzyl)carbamic acid t-butyl ester A dried 25 ml of two-neck round bottom flask was filled with argon gas. The solution of (4-amino-2-chloro-5-iodobenzyl)-carbamic acid t-butyl ester (268.4 mg, 0.70 mmol) in methylenechloride was put into the flask and then cooled to 0° C. To the solution were added methanesulfonylchloride (5 eq, 3.51 mmol, 271.91 μl) and TEA (3 eq, 2.10 mmol, 292.69 μl) slowly, and the mixture solution was stirred for 12 hours at room temperature. After confirming the completion of the reaction with TLC, the reaction was quenched with NaHCO₃ solution. The reaction solution was extracted with methylenechloride, washed with CuSO₄, water and brine, dried over Na₂SO₄, filtered and concentrated under reduced pressure. The obtained liquid was diluted with the solution (THF: H₂O=2:1), added NaOH (5 eq, 3.5 mmol, 140 mg) and stirred for 1 hour. After confirming the completion of the reaction with TLC, the reaction solution was acidified by 10% HCl, extracted with ethylacetate, washed with water and brine, dried over Na₂SO₄, filtered and concentrated under reduced pressure. The obtained liquid was purified with column chromatography (n-hexane/ethyl acetate=2/1) to yield a white solid (211.8 mg, 65.53%).

mp: 150~152° C.;

IR (KBr pellet, cm⁻¹): 3372, 2986, 1693, 759;

¹H NMR (400 MHz, CDCl₃): δ7.75 (s, 1 Hz), 7.59 (s, 1 Hz), 6.71 (bs, 1 Hz), 5.09 (bs, 1H) 4.29 (d, 2H, J=6.0 Hz), 3.00 (s, 3 Hz), 1.42 (s, 9 Hz)

Step 5: N-(4-aminomethyl-5-chloro-2-Iodophenyl) methanesulfonamide (2-chloro-5-iodo-4-methanesulfonylamino-benzyl)-carbamic acid isopropyl ester (100 mg, 0.22 mmol) was put into a dried 25 ml of round-bottom flask and dissolved in methylenechloride. To the solution were added 5-6 drops of CF₃COOH and stirred for 12 hours. After confirming the completion of the reaction with TLC, the resulting solution was concentrated under reduced pressure using toluene to yield a brown syrup (102.1 mg, 130.48%).

¹H NMR (400 MHz, CD₃OD): δ8.05 (s, 1H)), 7.59 (s, 1H), 4.19 (s, 2H)), 3.05 (s, 3H)

Step 6: N-4-[3-(4-t-butylbenzyl)ureidomethyl]-5-chloro-2-iodophenyl methanesulfonamide A dried 25 ml of two-neck round bottom flask was filled with argon gas and the solution of 4-t-butyl-benzylamine (34.28 μl, 0.28 mmol) in methylenechloride was put into the flask. To the solution were added Boc₂O (1.5 eq, 0.32 mmol, 72.44 μl) and DMAP (0.2 eq, 0.01 mmol, 5.13 mg) slowly, and stirred for 5 hours. After confirming for 1-t-butyl-4-isocyanatomethyl-benzene to be produced with TLC, to the solution were added N-(4-aminomethyl-5-chloro-2-iodophenyl)-methanesulfonamide (1 eq, 0.28 mmol, 74.6 mg) and TEA (2 eq, 0.56 mmol, 58.54 μl), and stirred for 12 hours. After confirming the progress of the reaction, the reaction solution was extracted with methylenechloride, washed with water and brine, dried over Na₂SO₄, filtered and concentrated under reduced pressure. The obtained liquid was purified with column chromatography (n-hexane/ethyl acetate=1/1) to yield a white solid (30.4 mg, 20.04%).

mp: 163~165° C.

IR (KBr pellet, cm⁻¹):3319, 3024, 2961, 1638, 1315, 765;

¹H NMR (400 MHz, CDCl₃): δ 7.70 (s, 1H), 7.49 (s, 1H), 7.26 (d, 2H, J=8.4 Hz), 7.11 (d, 2H, J=8.0 Hz), 6.64 (s, 1H), 5.17 (bs, 2H), 4.25 (s, 2H), 4.22 (s, 2H), 2.92 (s, 3H), 1.21 (s, 9H).

EXAMPLE 19

N-{4-[3-(4-t-butylbenzyl)ureidomethyl]-2-ethyl-6-fluorophenyl}methanesulfonamide

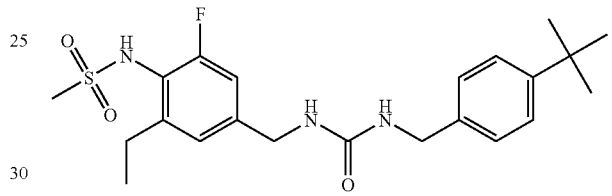

N-{4-[3-(4-t-butyl-benzyl)-ureidomethyl]-2-fluoro-6-vinyl-phenyl}methanesulfonamide (15.6 mg, 0.04 mmol) was dissolved in methanol. To the solution was added Pd/C (10 wt. %) and air in the flask was displaced with hydrogen gas. The reaction solution was stirred for 1 hour. After confirming the completion of the reaction with TLC, Pd/C was filtered off through celite. The methanol was removed under reduced pressure and column-chromatographed (n-hexane/ethyl acetate ~1/1) to yield a white solid (15.8 mg, 100.0%).

¹H NMR (400 MHz, CDCl₃): 7.28 (d, 2H, J=8.4 Hz), 7.15 (d, 2H, J=8.0 Hz), 6.91 (s, 1H), 6.84 (q, 1H, J=10.4 Hz), 5.86 (s, 1H), 4.28 (s, 4H), 3.00 (s, 3H), 2.76 (q, 2H, J=7.6 Hz), 1.23 (s, 9H), 1.31 (t, 3H, J=8.0 Hz).

EXAMPLE 20

N-{4-[3-(4-t-butylbenzyl)ureidomethyl]-2-fluorophenyl}methanesulfonamide

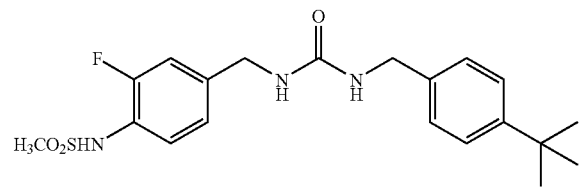

3-fluoro-4-methanesulfonylaminobenzylamine hydrochloride (1.13 g) prepared in step 3 of Example 1 was dissolved in DMF (6 mL) and diluted with dichloromethane (35 mL). To the solution were added 4-t-butylbenzylisocyanate (1.09 g) and TEA (1.2 mL) and stirred at room temperature for 2 hours. The reaction solution was concentrated under reduced pressure, diluted with ethylacetate (20 mL) and washed with water and saturated NaCl aqueous solution. The resulting solution was dried over anhydride MgSO₄ and the remaining liquid was concentrated under reduced pressure. The residue was purified with column chromatography (n-hexane/ethyl acetate=312) to yield title compound (1.23 g, 53%).

mp: 95° C.

$^1$H-NMR (CDCl$_3$+CD$_3$OD, 300 MHz) 1.23 (s, 9H), 2.91 (s, 3H), 4.22 (s, 2H), 4.24 (s, 2H), 6.99-6.93 (m, 2H), 7.13 (d, 2H, J=8.2 Hz), 7.26 (d, 2H, J=8.4 Hz), 7.34 (t, 1H, J=8.3 Hz)

LRMS (FAB): 408 (M+H+).

EXAMPLE 21

N-{4-[3-(4-t-butylbenzyl)ureidomethyl]-2-methylphenyl}methane sulfonamide

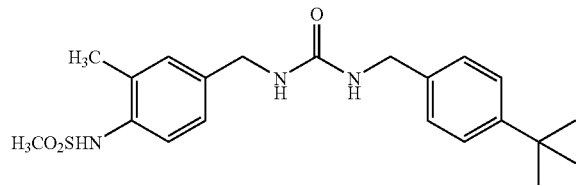

The N-{4-[3-(4-t-butylbenzyl)ureidomethyl]-2-methylphenyl}methane sulfonamide (22%) was synthesized according to the same procedure as described in Example 20.

$^1$H-NMR (300 MHz, CD$_3$OD): δ 1.29 (s, 9H), 2.33 (s, 3H), 2.94 (s, 3H), 4.28 (s, 4H), 7.35-7.09 (m, 7H) IR (neat) cm$^{-1}$: 3368, 2960, 1635, 1567, 1504, 1321. Mass (LC) 404.1 [M+H]+

EXAMPLE 22

N-{4-[3-(4-t-butylbenzyl)ureidomethyl]-2-chlorophenyl}methane sulfonamide

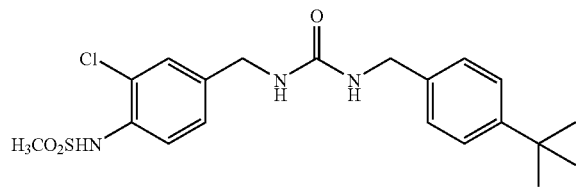

The N-{4-[3-(4-t-butylbenzyl)ureidomethyl]-2-chlorophenyl}methane sulfonamide (10%) was synthesized according to the same procedure as described in Example 20.

mp: 60-61° C.;

$^1$H-NMR (CDCl$_3$, 300 MHz): 1.29 (s, 9H), 2.97 (s, 3H), 4.35 (d, 4H, J=5.9 Hz), 4.64 (bs, 2H), 6.70 (bs, 1H), 7.23-7.15 (m, 3H), 7.36-7.31 (m, 3H), 7.57 (d, 1H, J=8.3 Hz);

IR (neat, cm$^{-1}$): 3353, 2960, 1635, 1571, 1496, 1329;

LRMS (ESI): m/z 424.0 (M+H+).

EXAMPLE 23

N-{4-[3-(4-t-butylbenzyl)ureidomethyl]-2-nitrophenyl}methane sulfonamide

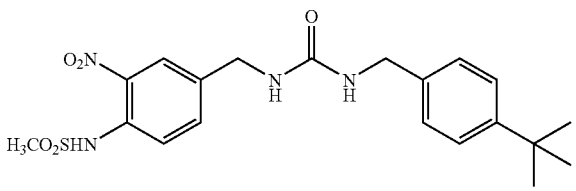

Step 1:
N-(4-cyano-2-nitrophenyl)methanesulfonamide

KH (700 mg, 6.1 mmol) was dissolved in THF (15 mL) at −78° C. and to the solution was added dropwise the solution of 4-amino-3-nitro-benzonitrile (500 mg, 3.1 mmol) in THF (10 mL). After the reaction solution was stirred for 30 minutes, to the solution was added dropwisely methanesulfonyl chloride (0.35 mL, 4.6 mmol) and stirred for 3 hours. The reaction solution was quenched with water and the resulting solution was diluted with ethylacetate. The organic phase was washed with water and brine, dried over anhydride MgSO₄ and concentrated under reduced pressure. The residue was purified with column chromatography (n-hexane/ethyl acetate=5/1) to yield the nitrile (120 mg, 16%).

$^1$H-NMR (300 MHz, CDCl$_3$): δ 3.24 (s, 3H), 7.90 (dd, 1H, J=8.8, 2.0 Hz), 8.03 (d, 1H, J=8.8 Hz), 8.59 (d, 1H, J=2.0 Hz)

Step 2: N-[4-(aminomethyl)-2-nitrophenyl]methanesulfonamide

The nitrile (120 mg, 0.50 mmol) was dissolved in THF (5.0 mL). To the solution was added dropwise the solution of 1M BH$_3$ (1.5 mL) in toluene and refluxed for 2 hours. To the solution was added 2N HCl (1.0 mL) and then refluxed for 1 hour. The resulting solution was concentrated under reduced pressure to yield crude amine (48 mg, 39%). The amine compound was used for step 3 without purification process.

Step 3: N-{4-[3-(4-t-butylbenzyl)ureidomethyl]-2-nitrophenyl}methane sulfonamide The amine compound prepared in step 2 was reacted with t-butylbenzyl isocyanate to yield the urea (10%) according to the same procedure as described in Example 20.

mp=177-178° C.;

$^1$H-NMR (CDCl$_3$, 300 MHz) 1.29 (s, 9H), 3.10 (s, 3H), 4.35 (d, 2H, J=5.7 Hz), 4.40 (d, 2H, J=5.9 Hz), 4.73 (bs, 1H), 4.81 (bs, 1H), 7.23 (d, 2H, J=8.3 Hz), 7.36 (d, 2H, J=8.4 Hz), 7.58 (d, 1H, J=6.6 Hz), 7.81 (d, 1H, J=8.8 Hz), 8.12 (s, 1H), 9.64 (bs, 1H).

IR (neat, cm$^{-1}$): 3317, 2958, 2927, 2860, 1632, 1534;

LRMS (ESI): m/z 435 (M+H+).

EXAMPLE 24

N-{4-[3-(4-t-Butyl-benzyl)-ureidomethyl]-2-iodo-phenyl}-methanesulfonamide

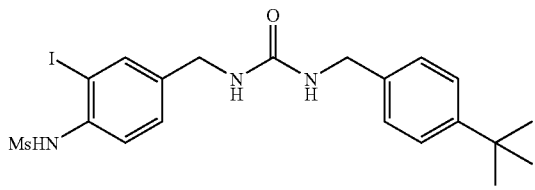

N-(4-Aminomethyl-2-iodo-phenyl)-methanesulfonamide and HCl salt (297 mg, 0.820 mmol) were reacted with (4-t-butyl-benzyl)-carbamic acid phenyl ester following the general procedure to give a white solid (152 mg).

$^1$H NMR (300 MHz, CDCl$_3$): 7.68 (d, 1H, J=1.8 Hz), 7.46 (d, 1H, J=8.1 Hz), 7.32 (m, 2H), 7.19~7.15 (m, 3H), 6.63 (br, 1H), 5.20 (dt, 2H, J=21 Hz), 4.27 (d, 2H, J=5.1 Hz), 4.22 (d, 2H, J=5.7 Hz), 2.95 (s, 3H), 1.28 (s, 9H). IR (neat, cm$^1$): 3322, 2962, 1634, 1566, 1487, 1384, 1327.

EXAMPLE 25

N-{4-[3-(4-t-Butyl-benzyl)-ureidomethyl]-2,6-difluoro-phenyl}-methanesulfonamide

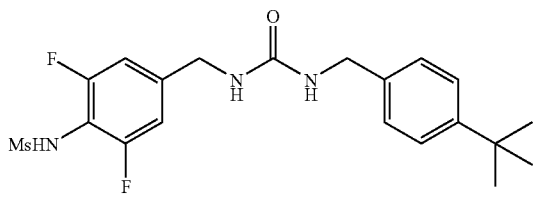

N-(4-Aminomethyl-2,6-difluoro-phenyl)-methanesulfonamide and HCl salt (100 mg, 0.36 mmol) were reacted with (4-t-butyl-benzyl)-carbamic acid phenyl ester following the general procedure to give a white solid (18 mg, 12%).

$^1$H NMR (300 MHz, CD$_3$OD): 7.29 (d, 2H, J=8.4 Hz), 7.17 (d, 2H, J=8.4 Hz), 6.98 (d, 2H, J=9.0 Hz), 6.17 (bt, 1H), 6.06 (bt, 1H), 4.32 (d, 2H, J=6.3 Hz), 4.26 (d, 2H, J=6.0 Hz), 3.03 (s, 3H), 1.23 (s, 9H).

EXAMPLE 26

N-{4-[3-(4-t-Butyl-benzyl)-ureidomethyl]-2,5-difluoro-phenyl}-methanesulfonamide

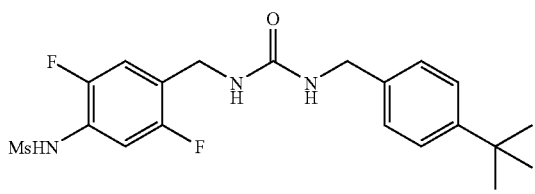

Step 1: (4-amino-2,5-difluorobenzyl)carbamic acid t-butyl ester

A dried 50 ml two-neck round bottom flask was filled with argon gas. The solution of 4-amino-2,5-difluorobenzonitrile (0.5 g, 3.24 mmol) in tetrahydrofuran was put into the flask and cooled to 0° C. To the solution was added Borane-THF complex (2 eq, 6.49 mmol, 6.49 ml) slowly. The temperature of the mixture was raised and heated to reflux for 18 hours. After confirming the completion of the reaction with TLC, to the solution was added methanol slowly (generation of bubbles) and stirred for 2 hours. The methanol was removed under reduced pressure and the residue was extracted with ethylacetate. The ethylacetate layer was washed with water, dried over MgSO$_4$, filtered, and concentrated under reduced pressure to yield yellow syrup. The above obtained liquid was dissolved in tetrahydrofuran and added BOC$_2$O (1.0 eq, 0.71 g) slowly and stirred for 12 hours at room temperature. After confirming the completion of the reaction with TLC, the reaction solution was extracted with ethylacetate, washed with water and brine, dried over MgSO$_4$, filtered and concentrated under reduced pressure. The obtained liquid was purified with column chromatography (n-hexane/ethyl acetate=4/1) to yield a white solid (0.43 g, 51.2%).

Step 2: (2,5-difluoro-4-methanesulfonylbenzyl)carbamic acid t-butyl ester

A dried 25 ml of two-neck round bottom flask was filled with argon gas. The solution of (4-amino-2,5-difluorobenzyl)-carbamic acid t-butyl ester (0.43 g, 1.66 mmol) in methylenechloride was put into the flask and then cooled to 0° C. To the solution were added methanesulfonylchloride (1.2 eq, 1.99 mmol, 0.16 ml) and pyridine (excess, 0.5 ml) slowly, the mixture solution was refluxed for 12 hours. After confirming the completion of the reaction with TLC, the reaction solution was acidified by 10% HCl, extracted with methylenechloride, washed with water and brine, dried over MgSO$_4$, filtered and concentrated under reduced pressure. The obtained liquid was purified with column chromatography (n-hexane/ethyl acetate=2/1) to yield a white solid (0.41 g, 73.5%).

$^1$H NMR (300 MHz, CDCl$_3$): δ 7.32 (m, 1H), 7.19 (m, 1H), 6.72 (bs, 1H), 4.95 (bs, 1H), 4.30 (d, 2H, J=6.3 Hz), 3.05 (s, 3H), 1.46 (s, 9H)

Step 3: 2,5-difluoro-4-methanesulfonylbenzylamine hydrochloride (2,5-difluoro-4-methanesulfonylbenzyl)carbamic acid t-butyl ester (0.41 g, 1.22 mmol) was put into the 50 ml one-neck round bottom flask and was poured with 30 ml 1,4-dioxane. To the solution was added c-HCl (excess, 2 ml) and stirred for 4 hours. After confirming the completion of the reaction with TLC, the reaction solution was concentrated under reduced pressure. The obtained solid was washed with ethylacetate and filtered with glass filter. The obtained solid was dried in a air to yield a solid (0.24 g, 72.5%).

Step 4: N-{4-[3-(4-t-Butyl-benzyl)ureidomethyl]-2,5-difluoro-4-methanesulfonylphenyl}methanesulfonamide 2,5-difluoro-4-methanesulfonylbenzylamine hydrochloride (70 mg, 0.26 mmol) and 4-t-butylbenzylcarbamic acid phenyl ester (1.1 eq, 80 mg) were put into the 25 ml one-neck round bottom flask and poured with 15 ml acetonitrile. To this solution was added triethylamine (excess, 0.5 ml) and stirred for 18 hours. After confirming the completion of the reaction with TLC, the reaction solution was concentrated under reduced pressure. The obtained substance was extracted with methylene chloride and washed with 1M HCl solution, dried over MgSO$_4$, filtered and concentrated under reduced pressure. The obtained liquid was column-chromatographed (n-hexane/ethyl acetate=2/3) to yield title compound (64 mg)

$^1$H NMR (300 MHz, CDCl$_3$): 7.35 (d, 2H, J=8.1 Hz), 7.29 (m, 1H), 7.23 (m, 2H), 7.14 (m, 1H), 6.78 (s, 1H), 4.84 (m, 2H), 4.34 (m, 4H) 3.02 (s, 3H), 1.30 (s, 9H).

EXAMPLE 27

N-{4-[3-(4-t-Butylbenzyl)ureidomethyl]-2-chloro-6-methylphenyl}methanesulfonamide

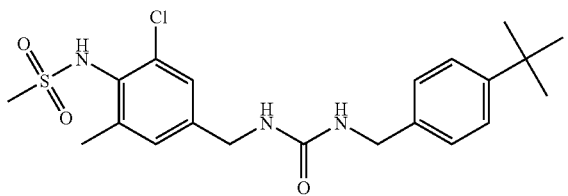

After 4-t-Butyl-benzylamine (1.5 eq, 72.85 µl, 0.45 mmol) was dissolved in methylene chloride, BOC$_2$O (1.5 eq, 0.45 mmol, 103.49 µl) and DMAP (0.2 eq, 0.06 mmol, 7.33 mg) were added into the mixture. The reaction mixture was stirred for 5 hrs. After confirming the synthesis of the 1-t-Butyl-4-isocyanatomethyl-benzene with TLC, N-(4-Aminomethyl-2-chloro-6-methyl-phenyl)-methanesulfonamide (1 eq, 0.30 mmol, 107.7 mg) and TEA (2 eq, 0.60 mmol, 83.63 µl) were added into the mixture. The reaction mixture was stirred for 12 hrs. The reaction solvent was removed in vacuo. The residue was extracted with methylene chloride. A combined organic layer was washed with H$_2$O and brine, dried with Na$_2$SO$_4$, and then concentrated in vacuo. The residue was purified with column chromatography (n-Hx:EA=1:1) to yield white solid (31.3 mg, 24%).

Melting point: 170~172° C.;

IR (KBr pellet, cm$^1$): 3325, 2961, 1624, 1572, 1319, 767;
$^1$H NMR (400 MHz, CD$_3$OD): δ 7.31 (d, 2H, J=8.4 Hz), 7.22 (d, 1H, J=1.6 Hz), 7.17 (d, 2H, J=8.4 Hz), 7.10 (d, 1H, J=1.2 Hz), 4.25 (d, 4H, J=6.4 Hz), 3.05 (s, 3H), 2.39 (s, 3H), 1.26 (s, 9H).

EXAMPLE 28

N-{4-[3-(4-t-Butylbenzyl)-ureidomethyl]-5-chloro-2-ethylphenyl}methanesulfonamide

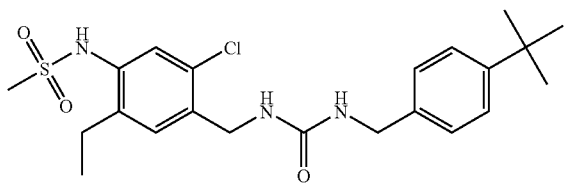

Step 1: (4-amino-2-chloro-5-trimethylsilanylethynyl-benzyl)carbamic acid t-butyl ester A dried 25 ml of two-neck round bottom flask was filled with argon gas and the solution of (4-amino-2-chloro-5-iodo-benzyl)-carbamic acid t-butyl ester (60 mg, 0.16 mmol), CuI (0.05 eq, 0.008 mmol, 1.52 mg) and PdCl$_2$(PPh$_3$)$_2$ in DMF was put into the flask. The solution was stirred at room temperature for 30 minutes. To the solution were added (TMS) acetylene (1.3 eq, 0.21 mmol, 29.39 mg) and triethylamine (3 eq, 0.48 mmol, 66.90 µl) and heated to reflux for 12 hours. After confirming the completion of the reaction with TLC, the resulting solution was extracted with ethylacetate, washed with water and brine, dried over Na$_2$SO$_4$, filtered and concentrated under reduced pressure. The obtained liquid was column-chromatographed (n-hexane/ethyl acetate=6/1) to yield an orange colored solid (44.9 mg, 81.17%).

mp: 104~106° C.;
IR (KBr pellet, cm$^{-1}$): 3356, 2962, 2143, 1698, 843;
$^1$H NMR (400 MHz, CDCl$_3$): 7.17 (s, 1H), 6.61 (s, 1H), 4.77 (bs, 1H), 4.14 (d, 2H, J=6.0 Hz), 1.35 (s, 9H), 0.15 (s, 9H).

Step 2: (2-chloro-5-ethynyl-4-methanesulfonylaminobenzyl)carbamic acid t-butyl ester A dried 25 ml of two-neck round bottom flask was filled with argon gas. The solution of (4-amino-2-chloro-5-trimethylsilanylethynyl-benzyl)-carbamic acid t-butyl ester (225.3 mg, 0.64 mmol) in methylenechloride was put into the flask and then cooled to 0° C. To the solution were added methanesulfonylchloride (5 eq, 3.20 mmol, 247.60 µl) and triethylamine (3 eq, 1.92 mmol, 267.61 µl) slowly and stirred at room temperature for 12 hours. After confirming the completion of the reaction with TLC, the reaction solution was quenched with NaHCO$_3$ solution. The reaction solution was extracted with methylenechloride, washed with CuSO$_4$, water and brine, dried over Na$_2$SO$_4$, filtered and concentrated under reduced pressure. The obtained liquid was diluted with the solution (THF:H$_2$O=2:1) and to the solution was added NaOH (5 eq, 3.20 mmol, 128 mg). The mixture was stirred for 1 hour. After confirming the completion of the reaction with TLC, the reaction solution was acidified by 10% HCl, extracted with ethylacetate, washed with water and brine, dried over Na$_2$SO$_4$, filtered and concentrated under reduced pressure. The obtained liquid was column-chromatographed (n-hexane/ethyl acetate=3/1) to yield a white solid (182.6 mg, 79.70%).

mp: 138~140° C.;
IR (KBr pellet, cm$^{-1}$): 3371, 3025, 2987, 1694, 1327, 701;
$^1$H NMR (400 MHz, CDCl$_3$): δ 7.53 (s, 1H), 7.40 (s, 1H), 6.99 (bs, 1H), 5.06 (s, 1H), 4.23 (d, 2H, J=6.0 Hz), 2.95 (s, 3H), 1.35 (s, 9H).

Step 3: N-(4-aminomethyl-5-chloro-2-ethynylphenyl)methanesulfonamide

A dried 25 ml of two-neck round bottom flask was filled with argon gas and the solution of (2-chloro-5-ethynyl-4-methanesulfonylamino-benzyl)-carbamic acid t-butyl ester (182.6 mg, 0.51 mmol) in methylenechloride was put into the flask. To the solution were added 5-6 drops of CF$_3$COOH and stirred for 12 hours. After confirming the completion of the reaction with TLC, the resulting solution was concentrated under reduced pressure using toluene to yield brown syrup (98.1 mg, 114.23%).

$^1$H NMR (400 MHz, CD$_3$OD): δ 7.69 (s, 1H), 7.66 (s, 1H), 4.22 (s, 2H), 4.04 (s, 1H), 3.03 (s, 3H).

Step 4: N-{4-[3-(4-t-butylbenzyl)ureidomethyl]-5-chloro-2-ethynyl phenyl}methanesulfonamide A dried 25 ml of two-neck round bottom flask was filled with argon gas and the solution of 4-t-butyl-benzylamine (44.08 #t, 0.27 mmol) in methylenechloride was put into the flask. To the solution were added Boc$_2$O (1.5 eq, 0.41 mmol, 93.14 μl) and DMAP (0.2 eq, 0.05 mmol, 6.59 mg) slowly and stirred for 5 hours. After confirming for 1-t-butyl-4-isocyanatomethyl-benzene to be produced with TLC, to the solution were added N-(4-aminomethyl-5-chloro-2-ethynyl-phenyl)-methanesulfonamide (1 eq, 0.27 mmol, 70 mg) and TEA (2 eq, 0.54 mmol, 75.27 μl) and stirred for 12 hours. After confirming the progress of reaction with TLC, the reaction solution was extracted with methylenechloride, washed with water and brine, dried over Na$_2$SO$_4$, filtered and concentrated under reduced pressure. The obtained liquid was column-chromatographed (n-hexane/ethyl acetate=1/1) to yield a white solid (20.20 mg, 16.73%).

mp: 116~118° C.

IR (KBr pellet, cm$^{-1}$): 3282, 3025, 2961, 2202, 1636, 1329, 762;

$^1$H NMR (400 MHz, CDCl$_3$): δ 7.53 (s, 1H), 7.46 (s, 1H), 7.27 (d, 2H, J=8.4 Hz) 7.14 (d, 2H, J=8.0 Hz), 6.91 (bs, 1H), 4.30 (s, 2H), 4.25 (s, 2H) 3.44 (s, 3H), 3.02 (s, 1H), 2.95 (s, 3H), 1.22 (s, 9H).

Step 5: N-{4-[3-(4-t-Butylbenzyl)-ureidomethyl]-5-chloro-2-ethylphenyl}methanesulfonamide N-{4-[3-(4-t-Butyl-benzyl)-ureidomethyl]-5-chloro-2-ethynyl-phenyl}-methanesulfonamide (30 mg, 0.19 mmol) and Lindler' catalyst were added in methanol. The reaction mixture was stirred under hydrogen atmosphere for 1 hr. The reaction mixture was filtered with Celite pad. The filterated was concentrated in vacuo and then purified with column chromatography (n-Hx:EtOAc=1:1) to yield yellow syrup (25.6 mg, 85%).

IR (NaCl neat, cm$^{-1}$): 3309, 3022, 2964, 1636, 1322, 1153, 757;

$^1$H NMR (400 MHz, CDCl$_3$): δ 7.22 (d, 2H, J=8.0 Hz), 7.18 (d, 1H, J=8.8 Hz), 7.08 (d, 2H, J=8.4 Hz), 7.00 (s, 1H), 6.91 (d, 1H, J=8.0 Hz), 6.63 (s, 1H), 5.26 (bs, 2H), 4.15 (d, 2H, J=10.8 Hz), 2.86 (s, 3H), 2.51 (q, 2H, J=7.6 Hz), 1.20 (s, 9H), 1.08 (t, 3H, J=7.6 Hz).

EXAMPLE 29

N-{4-[3-(4-t-Butyl-benzyl)-ureidomethyl]-2-fluoro-6-methyl-phenyl}-methanesulfonamide

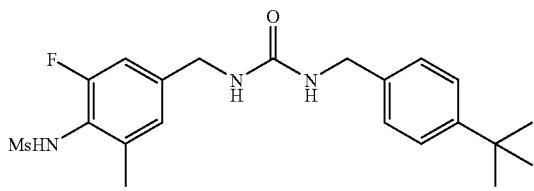

N-(4-Aminomethyl-2-fluoro-6-methyl-phenyl)-methanesulfonamide and HCl salt (200 mg, 0.70 mmol) were reacted with 3-(4-t-butyl-benzyl)-carbamic acid phenyl ester following the general procedure to give a white solid (31 mg, 11%).

1HNMR (300 MHz, DMSO-d6+CDCl$_3$): 8.70 (s, 1H), 7.25 (d, 2H, J=8.1 Hz), 7.14 (d, 2H, J=8.4 Hz), 7.04 (d, 1H, J=8.1 Hz), 7.02 (d, 1H, J=8.4 Hz), 5.55 (bs, 2H), 4.29 (s, 2H), 4.23 (s, 2H), 2.87 (s, 3H), 2.19 (d, 3H, J=2.7 Hz), 1.22 (s, 9H).

EXPERIMENTAL EXAMPLE

Biological Potency Test

1. $^{45}$Ca Influx Test

1) Separation of Spinal Dorsal Root Ganglia (DRG) in Newborn Rats and Primary Culture Thereof Neonatal (2-3 day old or younger than 2-3 day old) SD rats were put in ice for 5 minutes to anesthetize and disinfected with 70% ethanol. DRG of all part of spinal cord were dissected (Wood et al., 1988, J. Neurosci. 8, pp 3208-3220) and collected in DME/F12 medium to which 1.2 g/l sodium bicarbonate, 50 mg/l gentamycin were added. The DRG were incubated sequentially at 37° C. for 30 min in 200 U/ml collagenase and 2.5 mg/ml trypsin, separately. The ganglia were washed twice with DME/F12 medium supplemented with 10% horse serum, triturated through a fire-polished Pasteur pipette, filtered through Nitex 80 membrane to obtain single cell suspension and the suspension was washed once more. This was subjected to centrifugation, then resuspended in cell culture medium at certain level of cell density. As the cell culture medium, DME/F12 medium supplemented with 10% horse serum was diluted with identical medium conditioned by C6 glioma cells 2 days on a confluent monolayer (1:1), and NGF (Nerve Growth Factor) was added to adjust 200 ng/ml as final concentration. After the cells were grown 2 days in medium where cytosine arabinoside (Ara-C, 100 μM) was added to kill dividing nonneuronal cells, medium was changed to one without Ara-C. The resuspended cells were plated at a density of 1500-2000 neurons/well onto Terasaki plates previously coated with 10 μg/ml poly-D-ornithine.

2) $^{45}$Ca Influx Experiments

DRG nerve cells from the primary culture of 2 days were equilibrated by washing 4 times with HEPES (10 mM, pH 7.4)-buffered Ca$^{2+}$, Mg$^{2+}$-free HBSS (H-HBSS). The solution in each well was removed from the individual well. Medium containing the test compound plus capsaicin (final concentration 0.5 μM) and $^{45}$Ca (final concentration 10 μCi/ml) in H-HBSS was added to each well and incubated at room temperature for 10 mins. Terasaki plates were washed five times with H-HBSS and dried at room temperature. To each well, 0.3% SDS (10 μl) was added to elute $^{45}$Ca. After the addition of scintillation cocktail of into each well, the amount of $^{45}$Ca influx into neuron was measured by counting radioactivity. Antagonistic activities of test compounds against vanilloid receptor were calculated as percent of the inhibition of maximal response of capsaicin at a concentration of 0.5 μM. In summary, all examples of the present invention showed good to excellent IC$_{50}$ values between 40 and 500 nM, with most of the compounds having a IC50 values below 600 nM.

TABLE 1

Results of Calcium Influx Test

| Examples | Calcium Uptake Test (IC$_{50}$, μM) |
|---|---|
| 1 | 0.49 |
| 2 | 0.26 |
| 3 | 0.29 |
| 4 | 0.31 |
| 5 | 0.21 |
| 6 | 0.35 |
| 7 | 0.36 |
| 8 | 0.18 |
| 9 | 0.36 |
| 10 | 0.44 |
| 11 | 0.046 |
| 12 | 0.12 |
| 13 | 0.15 |
| 14 | 0.041 |
| 15 | 0.59 |
| 16 | 0.10 |
| 17 | 0.29 |
| 18 | 0.53 |
| 19 | 0.15 |
| 20 | 0.30 |
| 21 | 0.083 |
| 22 | 0.24 |
| 23 | 0.24 |
| 24 | 0.39 |
| 25 | 0.47 |
| 26 | 0.56 |
| 27 | 0.19 |
| 28 | 0.29 |
| 29 | 0.073 |

2. Analgesic Activity Test: Mouse Writhing Test by Inducing with Phenyl-p-quinone Male ICR mice (mean body weight 25 g) were maintained in a controlled lighting environment (12 h on/12 h off) for experiment. Animals received an intraperitoneal injection of 0.3 ml of the chemical irritant phenyl-p-quinone (dissolved in saline containing 5% ethanol to be a dose of 4.5 mg/kg) and 6 mins later, the number of abdominal constrictions was counted in the subsequent 6 mins period. Animals (10 animals/group) received 0.2 ml of test compounds solution in vehicle of ethanol/Tween 80/saline (10/10/80) intraperitoneally 30 min before the injection of phenyl-p-quinone. A reduction in the number of writhes responding to the test drug compound relative to the number responding in saline control group was considered to be indicative of an analgesic effect. Analgesic effect was calculated by % inhibition equation (% inhibition=(C−T)/C×100), wherein C and T represent the number of writhes in control and compound-treated group, respectively (Table 2).

TABLE 2

Test result of analgesic activity for writhing by phenyl-p-quinone

| Example | Dose (mg/kg) | Analgesic effect (% Inhibition) |
|---|---|---|
| 11 | 1 | 56 |
| 14 | 1 | 42 |
| 20 | 1 | 82 |
| 21 | 1 | 58 |
| 29 | 1 | 54 |

INDUSTRIAL APPLICABILITY

As explained above, the compound according to the present invention is useful to preventing and treating of pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, and heart disease etc.

More specifically, the compound according to the present invention is useful to preventing and treating of acute pain, chronic pain, neuropathic pain, post-operative pain, rheumatic arthrodynia, osteoarthritis pain, postherpetic neuralgia, diabetic neuropathy, HIV-related neuropathy, neurodegeneration, stroke, neurotic/allergic/inflammatory skin disease, psoriasis, pruritus, prurigo, asthma, chronic obstructive pulmonary disease, urinary incontinence, inflammatory bowel disease, hyperacusis, tinnitus, vestibular hypersensitiveness, and inotropic ischemia.

The invention claimed is:

1. A compound of the formula (Ia), or an isomer or pharmaceutically acceptable salt thereof;

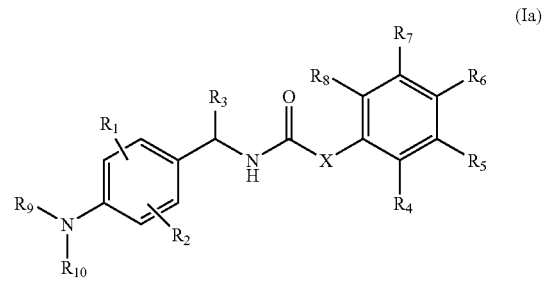

(Ia)

wherein,

X is $CR_{11}$=$CR_{12}$, or C≡C, wherein, $R_{11}$ and $R_{12}$ are independently hydrogen, halogen, C1-C5 alkyl, or phenyl;

$R_1$ and $R_2$ are independently hydrogen, carboxy, C1-C5 alkyl, halogen, nitro, C1-C5 alkoxy, halo (C1-C5) alkyl, C1-C5 alkylcarbonyl, C1-C5 alkylcarbonylamino, C1-C5 alkylsulfonylamino, phenylsulfonylamino, C1-C5 alkylthio, C1-C5 alkylsulfonyl, or C1-C5 alkoxycarbonyl;

$R_3$ is hydrogen, C1-C5 alkyl, C1-C5 alkoxy, or halo (C1-5)alkyl;

$R_4$, $R_5$, $R_6$, $R_7$, and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkyl carbonyl, C1-C5 alkoxycarbonyl, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkyl carbonyl, C1-C5 alkylthio, C1-C5 alkylsulfonyl, or C1-C5 alkoxy carbonyl;

$R_9$ is C1-C5 alkylsulfonyl or C2-C5 alkenylsulfonyl; and $R_{10}$ is hydrogen;

provided that if $R_3$ is different from hydrogen, then $R_{11}$ and $R_{12}$ are not simultaneously hydrogen.

2. A compound according to claim 1, or an isomer or pharmaceutically acceptable salt thereof;

wherein,

X is $CR_{11}$=$CR_{12}$ or C≡C, wherein, $R_{11}$ and $R_{12}$ are independently hydrogen, fluoro, bromo, chloro, iodo, methyl, ethyl, or propyl;

$R_1$ and $R_2$ are independently hydrogen, methyl, ethyl, propyl, fluoro, chloro, bromo, nitro, trifluoromethyl, methoxy, or ethoxy;

$R_3$ is hydrogen, methyl, ethyl, or methoxy;

$R_4$, $R_5$, $R_6$, $R_7$ and $R_8$ are independently hydrogen, carboxy, methyl, ethyl, propyl, isopropyl, butyl, t-butyl, sec-butyl, nitro, ethenyl, propenyl, methoxy, ethoxy, propoxy, C2-C5 alkynyl, trifloromethyl, methylthio, acetyl, methoxycarbonyl, phenyl, bromo, chloro, or iodo, wherein, phenyl may be unsubstituted or substituted with one or more substituent selected from carboxy, C1-C5 alkyl, halogen, nitro, C2-C5 alkenyl, C1-C5 alkoxy, halo (C1-C5)alkyl, C1-C5 alkylcarbonyl, C1-C5 alkylthio, C1-C5 alkylsulfonyl, or C1-C5 alkoxycarbonyl;

$R_9$ is methanesulfonyl, ethanesulfonyl, or ethenylsulfonyl; and $R_{10}$ is hydrogen;

provided that if $R_3$ is different from hydrogen, then $R_{11}$ and $R_{12}$ are not simultaneously hydrogen.

3. A compound according to claim 1, or an isomer or pharmaceutically acceptable salt thereof;
wherein,
X is trans $CR_{11}=CR_{12}$ or $C\equiv C$, wherein, $R_{11}$ and $R_{12}$ are independently hydrogen or methyl;

$R_1$ is hydrogen, methyl, ethyl, propyl, fluoro, chloro, bromo, iodo, nitro, methoxy, or ethoxy;

$R_2$ is hydrogen, methyl, fluoro, or chloro;

$R_3$ is hydrogen;

$R_4$, $R_5$, $R_7$, and $R_8$ are independently hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_6$ is halo (C1-C3) alkyl, isopropyl, or t-butyl;

$R_9$ is methanesulfonyl; and $R_{10}$ is hydrogen.

4. A compound according to claim 1, or an isomer or pharmaceutically acceptable salt thereof;
wherein, X is trans $CR_{11}=CR_{12}$ or $C\equiv C$, wherein, $R_{11}$ and $R_{12}$ are independently hydrogen or methyl;

$R_1$ is hydrogen, methyl, ethyl, propyl, fluoro, chloro, bromo, or iodo;

$R_2$ is hydrogen, methyl, fluoro, or chloro;

$R_3$ is hydrogen;

$R_4$ is hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_5$, $R_7$ and $R_8$ are all hydrogen;

$R_6$ is isopropyl or t-butyl;

$R_9$ is methanesulfonyl; and $R_{10}$ is hydrogen.

5. A compound according to claim 1, or an isomer or pharmaceutically acceptable salt thereof;
wherein
X is $CR_{11}=CH$, $CH=CR_{12}$, $CR_{11}=CR_{12}$, or $C\equiv C$, wherein $R_{11}$ and $R_{12}$ are both methyl;

$R_1$ is hydrogen, methyl, ethyl, propyl, fluoro, chloro, bromo, iodo, nitro, methoxy or ethoxy;

$R_2$ is hydrogen, methyl, fluoro, or chloro;

$R_3$ is methyl;

$R_4$, $R_5$, $R_7$ and $R_8$ are independently hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_6$ is halo (C1-C3) alkyl, isopropyl, or t-butyl;

$R_9$ is methanesulfonyl; and $R_{10}$ is hydrogen.

6. A compound according to claim 1, or an isomer or pharmaceutically acceptable salt thereof;
wherein X is $CR_{11}=CH$ or $C\equiv C$, wherein $R_{11}$ is methyl;

$R_1$ is hydrogen, methyl, ethyl, propyl, fluoro, chloro, bromo, or iodo;

$R_2$ is hydrogen, methyl, fluoro, or chloro;

$R_3$ is methyl;

$R_4$ is hydrogen, carboxy, methyl, ethyl, propyl, isopropyl, butyl, t-butyl, sec-butyl, nitro, ethenyl, propenyl, methoxy, ethoxy, propoxy, ethynyl, propynyl, trifloromethyl, methylthio, acetyl, methoxycarbonyl, bromo, chloro, or iodo;

$R_5$, $R_7$ and $R_8$ are all hydrogen;

$R_6$ is isopropyl or t-butyl;

$R_9$ is methanesulfonyl; and $R_{10}$ is hydrogen.

7. A compound according to claim 1, or an isomer or pharmaceutically acceptable salt thereof;
wherein $R_1$ is bound to the phenyl ring in the ortho position with respect to the sulfonyl amino group such that the compound has the formula (Ib)

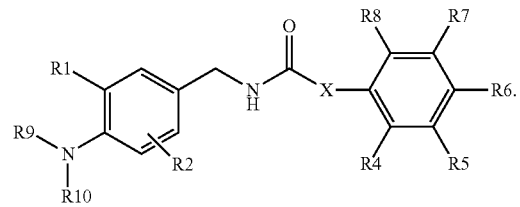

(Ib)

8. A compound according to claim 1, or an isomer or pharmaceutically acceptable salt thereof, wherein the compound is selected from the group consisting of 3-(4-t-butyl-phenyl)-N-(4-methanesulfonylamino-benzyl)-2-methyl-acrylamide, 3-(4-t-butyl-phenyl)-N-(3-fluoro-5-iodo-4-methanesulfonylamino-benzyl) acrylamide, 3-(4-t-butyl-phenyl)-N-(4-methanesulfonylamino-benzyl)propiolicamide, (E)-3-(4-t-butyl-phenyl)-N-(3-fluoro-4-methanesulfonylamino-benzyl)acrylamide, 3-(4-t-butyl-phenyl)-N-(3-chloro-4-methanesulfonylamino-benzyl)acrylamide, 3-(4-t-butyl-phenyl)-N-(3-methyl-4-methanesulfonylamino-benzyl)acrylamide, 3-(4-t-butyl-phenyl)-N-(3,5-difluoro-4-methanesulfonylamino-benzyl)acrylamide, 3-(4-t-butyl-phenyl)-N-(2,5-difluoro-4-methanesulfonylamino-benzyl)acrylamide, 3-(4-t-butyl-phenyl)-N-(3-chloro-5-iodo-4-methanesulfonylamino-benzyl)acrylamide, 3-(4-t-butyl-phenyl)-N-(3-chloro-4-methanesulfonylamino-5-methyl-benzyl)acrylamide, 3-(4-t-butyl-phenyl)-N-(3-fluoro-4-methanesulfonylamino-5-methyl-benzyl)acrylamide, 3-(4-t-butyl-phenyl)-N-(3-fluoro-4-methanesulfonylamino-benzyl)-2-methyl-acrylamide, 3-(4-t-butyl-phenyl)-but-2-enoic acid 3-fluoro-4-methanesulfonylamino-benzylamide,
3-(4-t-butyl-phenyl)-N-[1-(R)-(4-methanesulfonylaminophenyl)ethyl]propiolicamide,
3-(4-t-butylphenyl)-N-[1-(R)-(4-methanesulfonylaminophenyl)ethyl]-2-methylacrylamide, and
3-(4-t-butyl-phenyl)-N-[1-(3-fluoro-4-methanesulfonylaminophenyl)ethyl]-2-methyl-acrylamide.

9. A compound according to claim 1, or an isomer or pharmaceutically acceptable salt thereof, wherein the compound is selected from the group consisting of 3-(4-t-butyl-phenyl)-N-[1-(R)-(4-methanesulfonylaminophenyl)ethyl]-2-methylacrylamide,
3-(4-t-butyl-phenyl)-N-(3-fluoro-4-methanesulfonylamino-benzyl)-2-methyl-acrylamide,
3-(4-t-butyl-phenyl)-but-2-enoic acid 3-fluoro-4-methanesulfonylamino-benzylamide,
3-(4-t-butyl-phenyl)-N-[1-(R)-(4-methanesulfonylaminophenyl) ethyl]propiolicamide, and
3-(4-t-butyl-phenyl)-N-[1-(3-fluoro-4-methanesulfonylamino-phenyl)ethyl]-2-methyl-acrylamide.

* * * * *